United States Patent
Fikrig et al.

(10) Patent No.: US 10,092,626 B2
(45) Date of Patent: Oct. 9, 2018

(54) ANTI-INFECTIVE PROPERTIES OF ANTIFREEZE PROTEIN

(71) Applicant: Yale University, New Haven, CT (US)

(72) Inventors: Erol Fikrig, Guilford, CT (US); Martin Heisig, Marburg (DE); Nabil Abraham, New Haven, CT (US); Girish Neelakanta, Norfolk, VA (US)

(73) Assignees: Yale University, New Haven, CT (US); Howard Hughes Medical Institute, Chevy Chase, MD (US)

( * ) Notice: Subject to any disclaimer, the term of this patent is extended or adjusted under 35 U.S.C. 154(b) by 0 days.

(21) Appl. No.: 15/104,719

(22) PCT Filed: Dec. 17, 2014

(86) PCT No.: PCT/US2014/070894
§ 371 (c)(1),
(2) Date: Jun. 15, 2016

(87) PCT Pub. No.: WO2015/095349
PCT Pub. Date: Jun. 25, 2015

(65) Prior Publication Data
US 2016/0317618 A1 Nov. 3, 2016

Related U.S. Application Data

(60) Provisional application No. 61/917,326, filed on Dec. 17, 2013.

(51) Int. Cl.
*A61K 31/43* (2006.01)
*A61K 38/14* (2006.01)
*A61K 45/06* (2006.01)
*A61K 9/51* (2006.01)
*A61K 38/17* (2006.01)
*C08L 89/00* (2006.01)
*A61K 31/7036* (2006.01)
*A61K 31/7048* (2006.01)
*A61L 27/54* (2006.01)
*A61L 29/16* (2006.01)
*A61L 31/16* (2006.01)
*A61L 2/18* (2006.01)
*A61L 15/32* (2006.01)
*A61L 15/44* (2006.01)
*A61L 27/34* (2006.01)
*A61L 29/08* (2006.01)
*A61L 31/10* (2006.01)

(52) U.S. Cl.
CPC ............ *A61K 38/1767* (2013.01); *A61K 9/51* (2013.01); *A61K 31/43* (2013.01); *A61K 31/7036* (2013.01); *A61K 31/7048* (2013.01); *A61K 38/14* (2013.01); *A61K 45/06* (2013.01); *A61L 2/18* (2013.01); *A61L 15/32* (2013.01); *A61L 15/44* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *C08L 89/00* (2013.01); *A61L 2202/24* (2013.01); *A61L 2300/404* (2013.01); *A61L 2300/606* (2013.01); *A61L 2420/02* (2013.01)

(58) Field of Classification Search
CPC ............... A61K 2300/00; A61K 31/43; A61K 31/7036; A61K 31/7048; A61K 38/14; A61K 38/1767; A61K 45/06; A61K 9/51; A61L 15/32; A61L 15/44; A61L 2202/24; A61L 2300/404; A61L 2300/606; A61L 2420/02; A61L 27/34; A61L 27/54; A61L 29/085; A61L 29/16; A61L 2/18; A61L 31/10; A61L 31/16; C08L 89/00
USPC .................................................. 530/300, 325
See application file for complete search history.

(56) References Cited

U.S. PATENT DOCUMENTS

| | | | |
|---|---|---|---|
| 8,604,002 B1 | 12/2013 | Walters et al. | |
| 2004/0091966 A1* | 5/2004 | Zeidler | C12N 9/104 435/69.1 |
| 2010/0190690 A1 | 7/2010 | Spedden | |
| 2011/0171123 A1 | 7/2011 | Shirtliff et al. | |

OTHER PUBLICATIONS

Migliolo et al., Structural and functional analyses of a synthetic antibacterial and antifreeze peptide analogue. Annual Meeting of the Brazilian Biochemistry and Molecular Biology Society. May 2011. INISBR9774. Abstract.

Neelakanta et al., Anaplasma phagocytophilum induces Ixodes scapularis ticks to express an antifreeze glycoprotein gene that enhances their survival in the cold. J Clin Invest. Sep. 2010;120(9):3179-90. doi: 10.1172/JCI42868. Epub Aug. 25, 2010.

(Continued)

*Primary Examiner* — Julie Ha
(74) *Attorney, Agent, or Firm* — Wolf, Greenfield & Sacks, P.C.

(57) ABSTRACT

As microbial drug-resistance increases, there is a critical need for new classes of compounds to combat infectious diseases. The *Ixodes scapularis* tick antifreeze glycoprotein, IAFGP, functions as an anti-infective agent against diverse bacteria including methicillin-resistant *Staphylococcus aureus*. Recombinant IAFGP and a peptide, PI, described herein and derived from this protein, bind to microbes and alter biofilm formation. Transgenic iafgp-expressing flies and mice challenged with bacteria, as well as wild-type animals administered IAFGP or PI, were resistant to infection, septic shock, or biofilm development on implanted biomaterials. Antifreeze protein controls bacterial infection and present new therapeutic strategies to counter pathogens.

3 Claims, 24 Drawing Sheets
Specification includes a Sequence Listing.

(56) References Cited

OTHER PUBLICATIONS

Migliolo et al., Structural and functional characterization of a multifunctional alanine-rich peptide analogue from *Pleuronectes americanus*. PLoS One. 2012;7(10):e47047. doi: 10.1371/journal.pone.0047047. Epub Oct. 8, 2012.
International Preliminary Report on Patentability for PCT/US2014/070894 dated Jun. 30, 2016.

* cited by examiner

Figure 7A

```
  1 MTTLLRLTILIVAVAGVLG^SSKRAAR
 27             AATPATAATPATPATAAT
 45 PAI         AATPATAATPATAAT
 63 PARKAR      AATPATPATPATAATPATAAT
 90 PARKAR      AATAATPATPATAAT
111 PARKAR      AATPATPATAATPATAAT
135 PARKAR      AATPATPATAATPATAAT
159 PARKAR      AATPATPATAATPATAAT
183 PARKAR      AATPATPATAATAAT
204 PARKAR      AATAATPATPATAAT
225 PARKAR      AATPATAATAATPATAATAAA
```

Figure 7B

```
Peptide P1:    PARKARAATAATAATAATAATAAT
Peptide sP1:   AAAAATATAAARRAAAAPTTAKTT
```

ANTI-INFECTIVE PROPERTIES OF ANTIFREEZE PROTEIN

CROSS REFERENCED APPLICATION

This application is a national stage filing under 35 U.S.C. § 371 of international application number PCT/US2014/070894, filed Dec. 17, 2014, which was published under PCT Article 21(2) in English and claims the benefit under 35 U.S.C. § 119(e) of U.S. provisional application No. 61/917,326, filed Dec. 17, 2013, each of which is incorporated by reference herein in its entirety.

FUNDING

This invention was made with government support under Grant AI041440 awarded by National Institutes of Health. The government has certain rights in the invention.

BACKGROUND

Bacterial biofilms are a major concern in clinical medicine, with more than 400,000 estimated annual catheter-related blood stream infections in the US alone. Current treatments are unable to clear the majority of catheter-related infections. Thus, treatment is restricted to device removal and replacement, increasing the risk of re-infection and treatment costs. Additional approaches to treatment are needed.

SUMMARY

Described herein is a new class of anti-infectives that are effective against infectious agents, such as bacteria, viruses, fungi and protozoa. The subject anti-infectives include anti-freeze proteins and anti-freeze peptides from a variety of organisms and include synthetic proteins and peptides whose amino acid compositions are derived from anti-freeze proteins, such as from an arthropod anti-freeze protein. Anti-infectives include anti-freeze glycoproteins and glyco-peptides, such as *Ixodes scapularis* tick anti-freeze protein or peptide, including *Ixodes scapularis* tick glycoprotein and glyco-peptides. They are useful against a variety of organisms, such as bacteria, viruses, fungi and protozoa, in the body (e.g., the lungs, other organs) and on the skin by reducing (partially or completely) infection, such as by preventing its occurrence, reducing the extent to which it occurs or treating an existing infection. They reduce the ability of such infectious agents to infect by reducing (partially or completely/preventing) biofilm formation in the body (e.g., in the lungs, gastrointestinal tract, eyes, mucosal surfaces, or on other organs) or on the skin. Further described herein is the domain of the arthropod anti-freeze glycoprotein of the black-legged tick *Ixodes scapularis*, which is designated IAFGP, that reduces, partially or completely (prevents) biofilm formation. Also described are synthetic anti-infective peptides, such as synthetic anti-infective peptides that mimic the anti-infective function of IAFGP, and their design. In one embodiment, peptides that have anti-infective properties are peptides whose amino acid makeup mimic IAFGP amino acid sequence (are sufficiently similar in sequence to IAFGP or to other anti-freeze proteins or peptides, such as other anti-freeze glycoproteins or other anti-freeze glycopeptides, to have anti-infective function). In one example, the peptide is peptide P1, a synthetic peptide with homology to the arthropod anti-freeze protein IAFGP. Alternatively, the peptide is P0. As described, materials coated with an anti-infective peptide exhibit reduced bacterial biofilm formation after implantation of the material, such as in the form of a medical device (e.g., a catheter). In a surgical mouse model of catheter implantation, coating the catheter with peptide P1 reduced bacterial biofilm formation (e.g., *Staphylococcus aureus* biofilms by 95%).

The new class of anti-infectives described herein reduces (partially or completely) the effects of an infectious agent without direct killing of the infectious agent they reduce (partially or completely) bacterial colonization of a device without direct killing of bacterial pathogens. Without wishing to be bound by theory, in some embodiments, such anti-infectives exert their effects by reducing (partially or completely/preventing) biofilm formation, such as on surfaces of medical devices or other instruments/materials introduced into or in contact with the body. This provides a major advantage over other compounds, at least because development of resistance to the compounds will be delayed in the absence of lethal selection pressure on the bacteria. The sequence of such a peptide can be optimized, such as by changing the amino acid sequence (adding, deleting, substituting amino acid residue(s), which can be naturally occurring or non-naturally occurring) or by modifying the amino acid residues by addition of chemical compounds, such as those that increase binding to surfaces of materials introduced into or used on the body, such as surfaces of medical devices. The subject anti-infective peptides can be coated onto or attached to surface(s) of a medical device, such as a catheter or a wound cover (e.g., bandages) or embedded within material from which a medical device or wound cover is made (e.g., material from which catheters are made, such as plastic (PVC), latex rubber, polytetrafluoroethylene PTFE (Teflon) coated latex, vialon) and materials from which other medical devices are made.

Described herein are anti-infective proteins and anti-freeze peptides whose sequences are derived from an anti-freeze protein, such as an arthropod anti-freeze protein. Sequences are "derived from" anti-freeze protein in that the amino acid sequences are the same as a region of an anti-freeze protein or designed with reference to or based on that of an antifreeze protein, such as IAFGP. Anti-infective peptides include peptides whose sequences are the same as sequences in antifreeze protein that occur in an organism; peptides whose sequences are the same as (correspond to) a portion or fragment of the amino acid sequence of an antifreeze protein that occurs in an organism; peptides that exhibit sufficient homology or identity with antifreeze peptides, such as those whose sequences are presented herein, that they exhibit anti-infective properties similar to anti-freeze proteins that occur in an organism (e.g., at least 90% homology or identity); peptides whose amino acid sequences have been designed or modified with reference to the amino acid sequence of an antifreeze protein or portion or fragment of an antifreeze protein, which include peptides in which amino acid residues are naturally occurring or not naturally occurring or have been modified. In some embodiments, the anti-infective is a full-length antifreeze protein, which can be a full-length antifreeze protein that occurs in an organism or a modified full-length protein (e.g., a full-length protein whose amino acid sequence differs from a naturally-occurring antifreeze protein by at least one amino acid addition, deletion or substitution). In specific embodiments, anti-infective peptides are derived from the anti-freeze protein IAFGP or from corresponding sequences in other organisms. Such peptides include peptides whose amino acid sequences are not the same as (do not correspond to) but have been designed with reference to, a domain of IAFGP that reduces infective properties of organisms, such as bacteria, as described herein. An example of such an anti-infective peptide is a peptide (P1) whose sequence is derived from (with reference to) IAFGP from *Ixodes scapularis*. In some embodiments, an anti-infective peptide is a peptide having the amino acid sequence of SEQ ID NO: 1 or an amino acid sequence at least 90% identical (90, 91, 92, 93, 94, 95, 96, 97, 98, 99, 100% identical) to SEQ ID NO: 1 or at least 90% homologous (90, 91, 92, 93, 94, 95, 96, 97, 98, 99, 100% homologous) to SEQ ID NO: 1 or is a peptide having the amino acid of SEQ ID NO: 2 or an amino acid sequence at least 90% identical (90, 91, 92, 93, 94, 95, 96, 97, 98, 99, 100% identical) to SEQ ID NO: 2 or at least 90% homologous (90, 91, 92, 93, 94, 95, 96, 97, 98, 99, 100% homologous) to SEQ ID NO: 2. An anti-infective peptide can be at least 90% identical (90, 91, 92, 93, 94, 95, 96, 97, 98, 99, 100% identical) to peptide P1 or to peptide P2 or any other peptide whose sequence is provided herein or at least 90% homologous (90, 91, 92, 93, 94, 95, 96, 97, 98, 99, 100% homologous) to) to peptide P1 or to peptide P2 or any other peptide whose sequence is provided herein.

Anti-infective peptides may be obtained from by a variety of means, including obtaining it from (removing it from) a protein that comprises the peptide; chemical synthesis; or recombinant expression. A peptide can be produced by recombination expression using known methods, such as expression in a host cell, from which it is isolated using known methods. In one embodiment, the peptide is recombinant IAFGP, such as recombinant IAFGP produced in *Escherichia* (*E.*) *coli* (e.g., purified without glycosylation from *E. coli*). Alternatively, a peptide can be synthesized using prokaryotic or eukaryotic expression systems or can be removed/cut from a longer sequence (e.g., from IAFGP from *Ixodes scapularis*) produced in cells, whether by naturally occurring cell mechanisms or by cells genetically engineered to contain encoding nucleic acids (DNA, RNA). Other peptides, including peptides of the native IAFGP protein or peptides whose sequence is sufficiently similar to that of the P1 peptide that they reduce, partially or completely, infection, such as by reducing biofilm formation by an infectious agent, can also be used. Other peptides, such as peptides from an organism with the capacity to survive at low temperatures, can be identified by the methods described herein or by other methods and can also be used in methods and compositions described herein. For example, antifreeze glycoproteins with homology to IAFGP have been identified in some cold-water fish species (see, for example, Garner el at. (2010) *Chembiochem: a European journal of chemical biology*) and cold-exposed arthropods such as *Ixodes scapularis*.

Peptides described herein, such as P1 and P0, have properties that make each useful as anti-infectives. For example, in some embodiments, they are non-native sequences. They are typically small peptides (e.g., 10-50 amino acid residues), and can be chemically synthesized. In some embodiments, the anti-infective peptide has any number of amino acid residues from about 10 to about 50, such as 15, 16, 17, 18, 19, 20, 21, 22, 23, 24, 25, 26, 27, 28, 29, 30, up to and including 50 amino acid residues. In specific embodiments, they include 24 amino acid residues (e.g., P1, P0). In addition, they exhibit a broad spectrum of activity, including activity against Gram-positive and Gram-negative bacteria, including *Pseudomonas aeruginosa; Listeria monocytogenes; Staphylococcus aureus; Mycobacterium bovis*; and multiple additional infectious agents, including those in which the target of P1 and/or the target of P0 is present, which include multiple other clinically relevant bacterial pathogens. (see, for example, Cynes-Bentley et al. *PNAS* (2013)110:24).

Compositions comprising antifreeze peptides can be applied to material, such as material from which medical devices are made (e.g., catheter material), by a variety of methods, such as application methods that rely on spontaneous association of the peptide with catheter material or methods in which covalent binding occurs (which should extend duration of function). Coating of material can be carried out at the time of production of the material or a device from which it is made (e.g., at the time a catheter is made) or can be carried out afterwards, such as by applying compositions comprising antifreeze peptides at the time a device is used/introduced into a patient. Kits containing compositions comprising antifreeze peptides are also covered herein. Such kits can be used for coating a device or tissue.

There are numerous uses for the new class of anti-infectives (antifreeze peptides) described herein, such as peptide P1. For example, they can be used as a prophylactic coating for indwelling devices, such as intravenous catheters, heart valves, shunts, implants, prosthetic devices, and pacemakers or on external materials such as bandages, wound dressings or others. In other examples, the anti-infective peptides can be used as a prophylactic solution or treatment for external devices, such as contact lens. They can be used as anti-infectives/anti-biofilm agent in combination with antibiotics/conventional antimicrobial agents, such as ampicillin, kanamycin, streptomycin, gentamicin, erythromycin, vancomycin, daptomycin or catheter lock solutions. Further, antifreeze peptides and proteins can be used as a single anti-biofilm compound against mucoid infections like *Candida albicans, Klebsiella pneumonia* or *Pseudomonas aeruginosa* in cystic fibrosis patients (e. g., by being vaporized into the lungs) or to prevent biofilm formation on other organs or tissues.

Any of the compositions described herein may be used in therapy or in prophylaxis. Alternatively or in addition, the compositions may be for use as an anti-infective in vivo. In some embodiments, the composition is for use in a method of reducing the virulence of an infectious organism in vivo. In some embodiments, the composition is for use in a method of reducing or preventing biofilm formation in vivo. In some embodiments, the compositions are for use in a method for preventing or controlling bacterial disease. In some embodiments, the compositions are use in a method of treating infection associated with an implanted or indwelling medical device in a subject. In some embodiments, the compositions are for use in a method of reducing microbial colonization of a surface in a subject. In some embodiments, the surface is a surface of a medical device in the subject. In some embodiments, microbial colonization comprises biofilm formation.

Provided herein are ex vivo processes for producing a medical device, comprising coating a device with any of the compositions described herein. In some embodiments, the compositions described herein are in combination with one or more conventional antimicrobial agents. Also provided are medical devices coated with any of the compositions described herein. Also provided are uses of any of the compositions described herein for the manufacture of a medicament for use in a method as also defined herein.

Other advantages, features, and uses of the invention will be apparent from the Detailed Description of the Invention, the Drawings, and the Claims.

BRIEF DESCRIPTION OF THE DRAWINGS

The accompanying drawings are not intended to be drawn to scale. For purposes of clarity, not every component may be labeled in every drawing.

FIG. 1A shows binding between recombinant GST or GST-IAFGP with *Escherichia coli* (EC), *Serratia marcescens* (SM), *Pseudomonas entomophila* (PE), *Listeria monocytogenes* (LM), *Staphylococcus aureus* (SA). Bound protein was detected by immunoblot analysis. FIG. 1B shows GST-IAFPG binds insoluble *S. aureus* peptidoglycan. The peptidoglycan was incubated with recombinant GST or GST-IAFGP (input), respectively. The wash fractions (wash 1-3) and the peptidoglycan-containing pellet (associated) were probed for protein content by immunoblot analysis. Without protein incubation, the peptidoglycan showed no detectable signal (neg ctrl). FIG. 1C depicts biofilm formation of *S. aureus* cultures supplemented with GST or GST-IAFGP. Results are presented as the mean±SEM of 3 independent experiments performed in duplicate, with representative images of the stained biofilm below each column (One-Way-ANOVA with Tukey's post-test; ***: p<0.001; ns: not significant). FIG. 1D shows the exopolysaccharide formation by *S. aureus* supplemented with GST or GST-IAFGP as visualized by immunoblot analysis. Results are presented as the mean±SEM of 3 independent experiments (One-Way-ANOVA with Tukey's post-test; *: p<0.001; : p<0.01).

FIG. 2A shows P1 binding to various bacterial species. *S. aureus* SA113 (SA), the methicillin-resistant USA300 JE2 isolate (USA300), *L. monocytogenes* EGDe (LM), and *E. coli* DH5α (EC) were incubated with biotinylated P1 (pos ctrl) in DMSO. Following washing, bound peptide was detected by immunoblot. DMSO or *S. aureus* SA113 without peptide incubation served as negative controls. FIG. 2B depicts binding competition of P1, sP1 and IAFGP-GST to *S. aureus*. Bacteria were incubated with peptides followed by incubation with IAFGP-GST. Bound IAFGP was detected by immunoblot analysis. FIG. 2C shows biofilm formation by two *S. aureus* species supplemented with P1 or sP1. Results are presented as the mean±SEM of 3 independent experiments performed in duplicate, representative images of the biofilm stain below (One-Way-ANOVA with Tukey's post-test; ***: p<0.001; ns: not significant). FIG. 2D shows exopolysaccharide (PNAG) produced by two *S. aureus* species supplemented with P1 or sP1. PNAG was visualized using immunoblot analysis. Results are presented as the mean±SEM of 3 independent experiments, with representative images of the stained biofilm below (One-Way-ANOVA with Tukey's post-test; *: p<0.001; : p<0.01). FIG. 2E shows anti-biofilm activity of the native peptide P0.

FIG. 3A shows survival of Iafgp-transgenic and control flies (n=450) challenged with *S. aureus* SA113. Survival data were pooled from 6 independent experiments (Log-rank test; p<0.001). FIG. 3B shows colonization of iafgp-transgenic and control flies challenged with *S. aureus* SA113. Bacterial colonization of individual flies was determined by plating serial dilutions. Data was pooled from 3 independent experiments (One-Way-ANOVA with Tukey's post-test; *: p<0.001; : p<0.01; *: p<0.05). FIG. 3C presents PNAG production in iafgp-transgenic and control flies challenged with *S. aureus* SA113. PNAG levels of pools of 5 flies were assessed at different time points by immunoblot. Average signal intensities of 3 independent experiments±SEM with representative immunoblot images below are shown (Two-Way-ANOVA with Sidak's post test;***: p<0.01). FIG. 3D presents PNAG production in iafgp-transgenic and control flies challenged with *S. aureus* SA113. Paraffin sections of whole flies were stained for bacteria and PNAG. Black triangles point to bacteria, empty triangles indicate PNAG staining. FIG. 3E shows survival of iafgp-transgenic and control flies (n=150/180) challenged with *S. aureus* SA113 ΔicaADBC. Survival data were pooled from 4 independent experiments (Log-rank test; not significant).

FIGS. 4A, 4B and 4C present data from Iafgp-transgenic mice and wild-type animals that underwent cecal ligation and puncture surgery. FIG. 4A shows survival of the mice following cecal ligation and puncture surgery (Gehan-Breslow-Wilcoxon test; p<0.05). FIG. 4B presents body temperature of the mice (Two-Way ANOVA; p<0.001). FIG. 4C depicts disease scores for the animals (Two-Way ANOVA; p<0.01). Data were pooled from 6 independent experiments. Sham-treated animals were used as controls. FIG. 4D shows survival of iafgp-transgenic mice and wild-type animals challenged intranasally with USA300 JE2. Survival data represents one experiment (Log-rank-test; p<0.05). FIG. 4E shows the portion of C57Bl/6 and iafgp-transgenice mice that were live (black) and dead (light gray) following intranasal challenge with *S. aureus* USA300 JE2.

FIG. 5A depicts bacterial attachment to intravenous catheters that had been incubated in PBS, GST, GST-IAFGP, P2 and P21c before transferring into *S. aureus* SA113 suspensions. Bacterial attachment was quantified after sonication by plating serial dilutions. Data were pooled from 3 independent experiments (One-Way-ANOVA; *: p<0.05). FIG. 5B presents bacterial attachment to intravenous catheters that had been incubated in PBS, P1 or sP1 and implanted subcutaneously on the dorsal flanks of C57Bl/6 mice. 72 hrs after catheter inoculation with $5 \times 10^5$ CFU *S. aureus* SA113 the catheters were removed and the attached bacteria were quantified by plating serial dilutions. CFU data were pooled from 3 independent experiments (One-Way-ANOVA with Tukey's post-test; **: p<0.01). FIG. 5C shows scanning electron microscopic analysis of explanted catheters 72 h post inoculation in comparison to controls. *S. aureus* are indicated by black triangles, biofilm matrix are indicated by empty triangles.

FIGS. 7A-7B present amino acid sequences of IAFGP and example peptides. FIG. 7A presents the primary amino acid sequence of IAFGP (SEQ ID NO: 3) containing multiple repeats. The 251 amino acid IAFGP consists of a putative 26 amino acid secretion signal, with a predicted protease cleavage site between amino acid 19 and 20. The 225 N-terminal amino acids are organized in 10 repeats comprising 5-7 Ala-Ala-Thr (AAT) and Pro-Ala-Thr (PAT) triplets, interspersed by the 6 amino acid spacer sequence Pro-Ala-Arg-Lys-Ala-Arg (PARKAR, SEQ ID NO:30). AAT repeats are italic and PAT repeats are bold. The 57 triplets are predicted to be glycosylated on every threonine with a β-D-galactosyl-(1→3)-α-N-acetyl-D-galactosamine disaccharide. FIG. 7B presents amino acid sequences of peptides P0 (SEQ ID NO: 2); P6 (SEQ ID NO: 4); P1 (SEQ ID NO: 1) and sP1 (SEQ ID NO: 5). The sequence of P1 PARKARA-ATAATAATAATAATAAT (SEQ ID NO: 1), in which the triplets of P0 were replaced by 'AAT' triplets. The sequence of P0 is PARKARAATPATPATAATPATAAT (SEQ ID NO: 2). Anti-biofilm activity has been identified for peptide P0, which includes one native repeat of IAFGP.

FIG. 9A shows survival of female 5-9 day old iafgp-expressing or control fruit flies challenged with L. monocytogenes (n=40/60). A 0.6 μm tungsten needle was dipped into a 1:10 diluted stationary culture of L. monocytogenes and flies were pricked in the right lateral side of the thorax. Fly survival was monitored visually over the course of infection. Uninfected controls (n.i.; n=40) were pricked with a needle dipped into PBS. Data were pooled from 2 independent experiments (Log-rank test; p<0.005). FIG. 9B shows survival of 5-9 day old iafgp-expressing or control flies (n=400) upon oral challenge with S. marcescens. FIG. 9C shows survival of 5-9 day old iafgp-expressing or control flies (n=400) upon oral challenge with P. entomophila. Groups of 20-25 flies were transferred into vials containing only a piece of absorbing tissue. Stationary bacterial cultures, resuspended in 4% sucrose and diluted 2-fold were used to soak the paper, controls received only sucrose solution. Every 3 days the flies were transferred into new vials with freshly soaked tissue, and bacterial survival was measured. Iafgp-expressing flies demonstrated increased survival upon infection with S. marcescens or P. entomophila, two common fly pathogens. Uninfected controls (n.i.; n=40) were housed in vials with 4% sucrose. Data were pooled from 2 independent experiments (Log-rank test; p<0.001/p<0.001).

FIG. 12A shows gene expression of Diptericin. FIG. 12B shows gene expression of Drosomycin. Both Diptericin (5'-CCGCAGTACCCACTCAATCT-3' SEQ ID NO: 6 and 5'-ACTGCAAAGCCAAAACCATC-3'; SEQ ID NO: 7) and Drosomycin (5'-TACTTGTTCGCCCTCTTCG-3'; SEQ ID NO: 8 and 5'-GTATCTTCCGGACAGGCAGT-3'; SEQ ID NO: 9) are antimicrobial peptides (AMPs) involved in the immune response against gram-positive pathogens like S. aureus. Expression was quantified relative to the ribosomal protein 49 (5'-CCGCTTCAAGGGACAG-TATCTG-3' (SEQ ID NO: 31) and 5'CACGTTGTGCAC-CAGGAACTT-3'(SEQ ID NO:32)). Data were pooled from 2 independent experiments, each dot corresponds to the gene expression in one fly.

FIG. 14A shows cytokine levels of TNF-α. FIG. 14B shows levels of MCP-1. FIG. 14C shows levels of IL-12p40. FIG. 14D shows IL6 levels. Cytokines were measured in obtained samples using enzyme-linked immunosorbent assay (ELISA) kits (eBiosciences, San Diego, Calif.). TNF-α data were pooled from 3 independent experiments; MCP-1, IL-12p40 and IL6 were pooled from six independent experiments (One-Way-ANOVA with Tukey's post-test; ***: p<0.001).

DETAILED DESCRIPTION

Figure 1A:
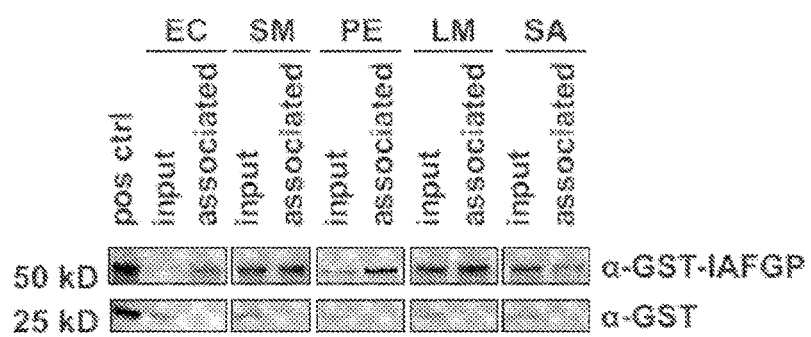
FIGS. 1A-1D show that IAFGP binds bacteria and alters microbial biofilm formation in vitro.

Diverse ectotherms tolerate the cold by altering the temperature at which their tissues freeze or by preventing the damage caused by the formation of ice (Clark et al. (2008) *J. Comp Physiol B*; Davies et al. (1997) *Curr Opin Struct Biol*; Doucet et al. (2009) *Cell and mol life sciences*). Major mechanisms of cold adaptation include accumulation of solvents to lower the freezing point and synthesis of antifreeze proteins (AFPs) that bind ice crystals (Davies et al. (1997) *Curr Opin Struct Biol*; Doucet et al. (2009) *Cell and mol life sciences*; Harding et al. (2003) *Euro J of Biochem*). AFPs prevent the growth of ice crystals in a non-colligative manner, lowering the freezing point of the solution (Sharp (2011) *PNAS*). Additional properties of AFPs include the inhibition of ice recrystallization or cell membrane stabilization at low temperatures (Davies et al. (1997) *Curr Opin Struct Biol*; Venketesh et al. (2008) *Critical Reviews in Biotech*.). Antifreeze glycoproteins (AFGPs), a class of AFPs, are characterized by canonical Ala-Ala-Thr or Pro-Ala-Thr repeats with a β-D-galactosyl-(1→3)-α-N-acetyl-D-galactosamine disaccharide attached to each threonine (Carvajal-Rondanelli et al. (2011) *J Sci Food Agric*). IAFGP is 251 amino acids, includes highly repetitive sequence, is highly glycosylated in vivo and presumed to be associated with the extracellular side of cell membranes. In Arctic fish, AFGPs contain between 4 to 55 repeats and AFGPs of different length may synergize, suggesting functional differences encoded into the number of tripeptide repeats and spacer sequences between them (Harding et al. (2003) *Euro J of Biochem*; Garner el at. (2010) *Chembiochem: a European journal of chemical biology*; Peltier et al. (2010) *Chemical Science*).

*Ixodes scapularis* ticks are seasonally exposed to cold temperatures in northern latitudes (Brownstein et al. (2003) *Environ Health Perspect*; Yuval et al. (1990) *J Med Entomol*). Iafgp-expression in ticks and in iafgp-transgenic fruit flies correlated with increased survival at low temperatures (Neelakanta et al. (2010) *J Clin Invest*; Neelakanta et al. (2012) *PLoS One*). Interestingly, iafgp-expression in the tick was up-regulated, both in the cold and upon infestation with a common *I. scapularis*-borne pathogen, *Anaplasma phagocytophilum*, the agent of human granulocytic anaplasmosis (Neelakanta et al. (2010) *J Clin Invest*). Expression of iafgp did not diminish the *A. phagocytophilum* burden within ticks (Neelakanta et al. (2010) *J Clin Invest*). Overall, these data suggest a form of mutualism, in which a microbe enhances the capacity of its arthropod vector to survive in the cold, thereby indirectly increasing its own potential to be transmitted to a vertebrate host. For some plant AFPs, chitinase or glucanase activity has been shown in vitro, suggesting that these proteins may have additional properties (Griffith et al. (2004) *Trends Plant Sci*; Zhang et al. (2007). *Z Naturforsch C*).

Described herein are antifreeze proteins, such as antifreeze glycoproteins (AFGPs), and peptides, also referred to as antifreeze peptides, with surprising anti-infective properties. Without wishing to be bound by theory, work described herein shows that they function at least by preventing exopolysaccharide/biofilm formation by an infectious agent, such as bacteria, fungi or protozoa; they can also provide beneficial function for viral infections.

Biofilms consist of various components, including a sugar-polymer-matrix, extracellular DNA and proteins. Resistance of bacteria that are inside biofilms against immune clearance and most antibiotics is increased by 100-1000 fold. They are a major cause of nosocomial infections; in the US annually about 400,000 bacterial blood-stream-infections are associated with intravenous catheters and biofilm formation on their surface. Eradication of biofilms is very difficult with drugs; usually, catheters are removed and replaced, but with the risk of reinfection.

Figure 15:
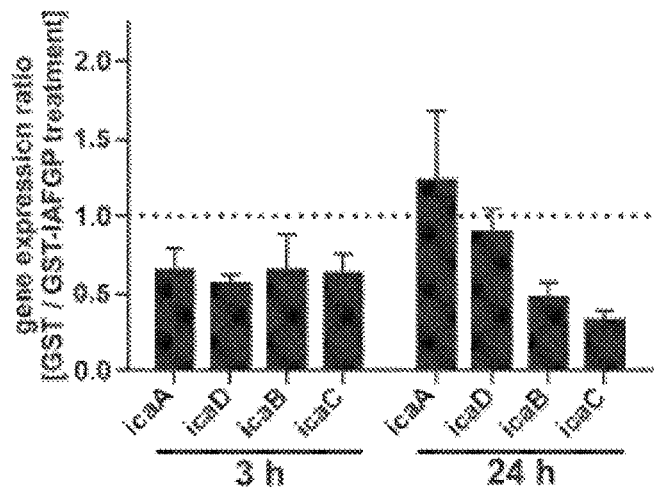
FIG. 15 shows that purified recombinant IAFGP has no effect on bacterial gene expression of genes involved in PNAG formation and secretion. A stationary culture of S. aureus SA113 was diluted 1:100 in BHI/G supplemented with 0.1 mg/ml recombinant IAFGP-GST or GST alone. Bacteria were incubated stationary at 37° C. and sampled at 3 h and 24 h. RNA was isolated using the RNAeasy kit (Qiagen, Hilden, Germany), reverse transcribed with iScript cDNA synthesis kit (BioRad, CA) and gene expression was quantified by qRT-PCR using iQ SYBR Green Supermix (BioRad, CA). Gene expression of the icaADBC operon, encoding the enzymes required for PNAG synthesis and assembly, was quantified relative to 16s rRNAP3-actin expression using oligomers 16sqRTF (5'-GGGACCCGCA-CAAGCGGTGG-3'; SEQ ID NO: 10), 16sqRTR (5'-GGGT-TGCGCTCGTTGCGGGA-3'; SEQ ID NO:19), icaAqRTF (5'-GAGGTAAAGCCAACGCACTC-3'; SEQ ID NO: 11), icaAqRTR (5'-CCTGTAACCGCACCAAGTTT-3'; SEQ ID NO: 12), icaDqRTF (5'-ACCCAACGCTAAAATCATCG-3'; SEQ ID NO: 13), icaDqRTR (5'-GCGAAAATGC-CCATAGTTTC-3'; SEQ ID NO: 14), icaBqRTF (5'-ATAC-CGGCGACTGGGTTTAT-3'; SEQ ID NO: 15), icaBqRTR (5'-TTGCAAATCGTGGGTATGTGT-3'; SEQ ID NO: 16), icaCqRTF (5'-CTTGGGTATTTGCACGCATT-3'; SEQ ID NO: 17), icaCqRTR (5'-GCAATATCATGCCGACACCT-3'; SEQ ID NO: 18). The ratios of gene expression following GST treatment divided by the gene expression following IAFGP treatment are shown. A ratio of 1 corresponds to similar gene expression in both treatment groups. Data show representative experiments performed in duplicate.

Recombinant IAFGP (purified without glycosylation from *Escherichia coli*) binds to multiple bacterial pathogens but does not elicit a bacteriocidal or bacteriostatic function (in vitro). As described herein, Iafgp-transgenic fruit flies show increased resistance to infection with *Staphylococcus aureus*, *Pseudomonas entomophila*, *Listeria monocytogenes* and *Serratia marcescens*. Further, Iafgp-transgenic mice show increased resistance to infection with methicillin resistant *Staphylococcus aureus* (MRSA) and to polymicrobial sepsis Bacterial binding of IAFGP correlated with inhibition of biofilm formation, which translated into increased host survival following bacterial challenge. Nearly 90% of the IAFGP sequence is composed of Ala-Ala-Thr and Pro-Ala-Thr motifs interrupted by spacer sequences. P1, which contains the prototypic Ala-Ala-Thr repeats, bound *S. aureus* in a manner similar to IAFGP and competitively inhibited IAFGP binding to the bacterial envelope, suggesting overlapping binding sites. Binding by IAFGP or P1 correlated with diminished exopolysaccharide (PNAG) in *S. aureus*, causing a reduction in bacterial biofilm formation. Since expression of genes encoding PNAG formation remained unchanged (FIG. 15) it is likely that IAFGP or P1 interferes with envelope- or membrane proteins, affecting cellular signaling or PNAG secretion and assembly.

Peptide P1 is a 24 amino acid peptide that is slightly positively charged and most likely binds to the (negatively charged) bacterial cell envelope through its positive charge. It prevents IAFGP binding to bacteria, which indicates that P1 has an identical (or overlapping) binding site as IAFGP on the bacterial surface. As described herein, it prevents *Staphylococcus aureus* biofilm formation in vitro and in vivo (MRSA isolates tested in vitro) and prevents *Staphylococcus aureus* PNAG formation (sugar component of the *S. aureus* biofilm) in vitro. P1 reduces *Staphylococcus aureus* biofilm formation on catheter materials in vivo by 95% and shows no signs of toxicity in vivo, under the conditions used.

*S. aureus* exopolysaccharide protects bacteria against attacks of the host response by inactivating phagocytic cells and providing a barrier against bactericidal compounds, such as AMPs or antibiotics (Nishimura et a. (2006) *J*

*Orthop Sci*; Vuong et al. (2004) *Cell Microbiol*). Iafgp-transgenic flies demonstrated increased survival following challenge with either gram-negative, *S. marcescens* and *P. entomophila*, or gram-positive, *L. monocytogenes* and *S. aureus*, pathogens. The lower bacterial burden in *S. aureus*-infected iafgp-transgenic flies was associated with a disturbance in biofilm formation, marked by elimination of detectable bacterial exopolysaccharide levels. This is consistent with in vitro data, described herein, on the alteration of biofilm development. The fly host pathogen-response did not play a role in this process; host phagocytosis, melanization, and antimicrobial peptide synthesis was not altered in iafgp-transgenic flies. In agreement with these findings, the exopolysaccharide-deficient *S. aureus* icaADBC-deletion mutant showed a similar pathogenicity in transgenic and control flies.

In warm-blooded animals a drop of the body core temperature results in tissue damage and death before tissues freeze. The first transgenic mice expressing an AFGP was generated to assess the anti-infective effect of IAFGP in mammals. In a model of polymicrobial sepsis, delayed disease onset in iafgp-expressing mice translated into a 40% extended survival time compared to controls. In addition, iafgp-expressing mice also exhibited increased survival after monomicrobial challenge with MRSA, demonstrating efficacy using a different manner of infection, and against a specific pathogen of clinical importance. *S. aureus* is also a frequent cause of catheter-related bloodstream infections, due in part to its ability to form persistent biofilms on artificial surfaces (Walz et al. (2010) *Journal of Intensive Care Medicine*; Walz et al. (2010) *J Intensive Care Med*; Otto (2008) *Curr Top Microbiol Immunol*). The influence of IAFGP or P1 on this process was examined (Kim et al. (2005) *J Biochem Mol Biol*; Rittirsch et al. (2009) *Nat Protoc*; Maki et al. (2006) *Mayo Clinic Proceedings*). Both IAFGP and P1 altered bacterial attachment to intravenous catheters in vitro; the peptide showed a more pronounced effect. This translated into substantial protection by P1 in the *S. aureus*-infected surgical catheter implant model, further demonstrating a potential application as prophylactic coating for catheters and other indwelling devices like heart valves, pacemakers or prosthetic implants. Recent studies showed that PNAG antisera protected mice against bacterial, fungal and protozoan pathogens in addition to *S. aureus*, suggesting that PNAG may also contribute to the virulence of other clinically relevant microbes (Cywes-Bentley et al. (2013) *PNAS*). IAFGP is effective against a broad spectrum of microorganisms; arthropods likely use this secondary function for protection against infection or to control their own microbiota.

Collectively, these data show that an antifreeze protein has antimicrobial activity, mediated by rendering the bacteria more susceptible to immune-clearance following reduction/prevention of biofilm formation. In ectotherms, low environmental temperatures cause a reduction of the body temperature, therefore limiting available energy due to diminished nutrient uptake and metabolic activity. As organisms cool, they become less effective at combatting pathogens (Bouma et al. (2013) *Dev Comp Immunol*; Triggs et al. (2012) *J Anim Ecol*). Moreover, when organisms warm after a period of cooling, they may be more susceptible to bacterial infection until they have sufficiently increased their temperature. From an evolutionary perspective, it would be beneficial if a molecule that facilitated survival in the cold also afforded protection against microorganisms. IAFGP represents the first example, and it will be interesting to determine whether other classes of antifreeze proteins also exhibit antimicrobial activity. These studies also have substantial practical implications, and suggest new therapeutic strategies to prevent or control bacterial disease in man, including infections associated with implanted biomaterials, either directly or in synergy with traditional antibiotics.

The surprising and unexpected anti-infective results presented herein show that antifreeze protein, such as IAFGP; truncated versions of IAFGP; and peptides derived from (whose sequences are based on) IAFGP, such as the P1 peptide derived from IAFGP, offer very useful therapeutic applications. Medical devices including implanted or indwelling medical devices, for example catheters, heart valves, shunts, or prosthetic implants, correlate with a high incidence rate of infection. Anti-infective peptides or compositions comprising anti-infective peptides may be used to reduce biofilm formation in or on any organ of the body, including mucosal surfaces (e.g., lungs, vaginal tract, gastrointestinal tract, sinuses). Application of compositions described herein as a coating or embedded within the device reduces biofilm formation on the device or in a wound and, thus, bacterial colonization and subsequent infection of the subject with the device is reduced (partially or completely). Additionally, to enhance the anti-infective effect of compositions described herein, it may be administered in combination with a conventional antimicrobial agent.

The peptides and compositions described herein may be coated, attached to, or embedded within any material known in the art to be useful in medical devices. In some embodiments, the peptides or compositions are in a solution (e.g., contact solution) used to treat or wash a medical device (e.g., contact lens). In other embodiments, the peptides or compositions are in a solution used to directly treat or wash a surface of the body, including the skin or a mucosal surface (e.g., lungs, vaginal tract, gastrointestinal tract, sinuses).

It will be evident to one of skill in the art that homologous genes or peptides for use in compositions described herein can be obtained from other species and can be identified by homology searches, for example through a protein BLAST search, available at the National Center for Biotechnology Information (NCBI) internet site (ncbi.nlm.nih.gov). Anti-infective peptides and anti-infective proteins can be produced using a variety of known methods, such as by expression in cells modified to contain nucleic acid (DNA, RNA) encoding the desired anti-infective peptide or anti-infective protein.

In some embodiments, an anti-infective peptide is a peptide having the amino acid sequence of SEQ ID NO: 1 or an amino acid sequence at least 90% identical (90, 91, 92, 93, 94, 95, 96, 97, 98, 99, 100% identical) to SEQ ID NO: 1 or at least 90% homologous (90, 91, 92, 93, 94, 95, 96, 97, 98, 99, 100% homologous) to SEQ ID NO: 1 or a peptide having the amino acid of SEQ ID NO: 2 or an amino acid sequence at least 90% identical (90, 91, 92, 93, 94, 95, 96, 97, 98, 99, 100% identical) to SEQ ID NO: 2 or at least 90% homologous (90, 91, 92, 93, 94, 95, 96, 97, 98, 99, 100% homologous) to SEQ ID NO: 2. An anti-infective peptide can be at least 90% identical (90, 91, 92, 93, 94, 95, 96, 97, 98, 99, 100% identical) to peptide P1 or to peptide P2 or any other peptide whose sequence is provided herein or at least 90% homologous (90, 91, 92, 93, 94, 95, 96, 97, 98, 99, 100% homologous) to peptide P1 or to peptide P2 or any other peptide whose sequence is provided herein.

In some embodiments, further optimization to reduce biofilm formation is achieved by modifying the sequence of the peptide or protein. In other embodiments, the sequence of the peptide or protein may be modified to enhance production of the peptide or protein. For example, a mutation can involve substitution, insertion, or deletion of one or more amino acids. In some embodiments, the peptide or protein comprises up to 4 (e.g. 1, 2, 3, or 4) amino acid residue variations/modifications relative to P1 (SEQ ID NO: 1) or P0 (SEQ ID NO: 2), and reduces biofilm formation.

Material and Methods

The following Materials and Methods were used in the work described herein (see, e.g., Examples 1-4).

Cloning, Expression and Purification of IAFGP.

Iafgp lacking the predicted secretion signal was PCR-amplified from pGEMT-iafgp using oligomers pGEX-F and pGEX-RL, digested with EcoRI and XhoI and cloned into pGEX-6p-3 (GE Healthcare, NJ), resulting in pGEX-iafgp. The sequence was confirmed before transformation into *E. coli* BL21 (Life Technologies, NY). Protein expression was induced with 1 mM IPTG for 3 h at 37° C. and bacteria were lysed using a French pressure cell press at 20,000 PSI. Following centrifugation, GST-IAFGP was affinity-purified using GST Sepharose (GE Healthcare, NJ), eluted (50 mM Tris-HCl, 10 mM reduced glutathione, pH 8.0) and stored in aliquots at −80° C. Precision protease treatment or dialysis resulted in IAFGP degradation. Therefore, the GST-tagged protein in elution buffer was used for experiments. Recombinant GST was purified from pGEX-6p-3 following the same protocol and used as a control.

Protein/Peptide Binding Assays and Immunoblot Analysis.

$1\text{-}2 \times 10^7$ bacteria in stationary growth phase were washed, resuspended in 100 µl PBS (Life Technologies, NY) and recombinant GST or GST-IAFGP was added (1.6 mM and 0.8 mM final concentration, respectively). Supernatant was removed after 10 min incubation at 37° C. and the pellet was washed 3 times in 0.1% Triton X100 (Sigma, MO) in PBS. Proteins were mixed with loading dye, heat denatured and size-separated by SDS-PAGE. Immunoblot using a polyclonal murine sera raised against GST-IAFGP or GST monoclonal antibody (Sigma, MO) was used for specific protein detection. The LI-COR Odyssey system was used to visualize IR-labeled secondary antibodies (LI-COR, NE). The impact of peptide pre-incubation on IAFGP binding to bacteria was investigated. Following incubation of washed bacteria for 30 min at 37° C. with 1 mg/ml peptide (KECK Biotechnology Resource Laboratory, CT; heat dissolved in PBS) the bacterial pellet was washed 3 times in 0.1% Triton X100 in PBS and IAFGP binding was assayed as described above. PNAG detection was performed as described in Crampton et al, but using a polyclonal rabbit antiserum against PNAG for detection[31,32].

Static Biofilm Assay.

Biofilm assays were performed as described[38]. Briefly, planktonic overnight cultures of *S. aureus* were diluted in glucose-supplemented tryptic soy broth or brain-heart-infusion broth (1% glucose; TSB/G or BHI/G) to $OD_{600}=0.015$ and distributed into 96 well plates (Corning, NC). After an 18 h incubation at 37° C. bacterial growth in each well was confirmed by the measurement of $OD_{600}$ using a spectrophotometer (BioTek, VT). The supernatant was discarded and the wells were washed with water twice. Bacteria associated with the well surface were dried and stained with safranin. The dye was then dissolved in 33% acetid acid and quantified at $OD_{415}$ nm using a spectrophotometer (BioTek, VT). Bacterial attachment to catheter materials pre-incubated with peptides was investigated. Vialon™ catheters (BD Biosciences, NJ) were incubated for 18 h in 0.1 mg/ml peptides dissolved in PBS, washed with PBS and incubated in bacterial suspensions for 24 h. Following removal of non-adherent bacteria with repeated washing, adherent bacteria and biofilms were dissociated using sonication in PBS. Bacterial titers were quantified by plating serial dilutions on agar plates and were calculated per as CFU per catheter.

Microscopy.

To visualize protein binding to the bacterial surface, GST and GST-IAFGP were fluorescently labeled using the kit according to the manufacturer's protocol. Stationary growth phase bacteria were washed once with PBS and incubated with labeled protein for 24 h at 37° C. Following washing and DAPI counterstain, bacteria were mounted on microscopic slides and investigated using a fluorescence microscope. Explanted catheters were fixed for 1 h at 23° C. in 4% Glutaraldehyde solution, washed three times in PBS and additionally fixed for 1 h at 23° C. in 2% Osmium tetroxide. Following repeated washing in water the samples were dehydrated in increasing concentrations of ethanol, critical point dried in liquid $CO_2$ and sputter coated (EMS, PA). Imaged were acquired using the ISIS SS40 SEM operating at 10 kV.

Mouse Immunization and Antibody Generation.

Polyclonal murine sera against recombinant GST-IAFGP were generated by subcutaneous immunization of female 6-8 week old Balb/c mice with 5 µg GST-IAFGP in Freund's complete adjuvant. Mice were boosted twice every 8-10 days with Freund's incomplete adjuvant and sacrificed 10 days after the final immunization. Polyclonal sera were used for detection of IAFGP.

Fly Propagation and Fly Infection.

Iafgp-expressing and mCherry-expressing flies were generated as described[13]. *D. melanogaster* flies were maintained using standard procedures[39]. The fly colony was sustained at 21-23° C. Following infection, flies were incubated at 29° C. to increase UAS-mediated transgene expression. Five to 9 day old females were used for experiments. Twenty to 30 flies per vial were infected by microinjection as reviewed in[40] and survival was monitored. Microinjection was performed into the thorax below the wing using a Nanojet microinjector (Drummond Scientific, PA). Bacteria in stationary growth phase were diluted in PBS to $OD_{600}=0.01$ or $OD_{600}=0.1$ and 9.2 nl were injected, corresponding to an infectious dose of 50-100 to 500-1000 CFU per fly respectively. For CFU analysis individual flies were homogenized in 500 µl PBS using a bullet blender (Nextadvance, NY) and steel beads. Serial dilutions were plated on brain-heart-infusion agar plates and incubated at 37° C. overnight. Endogenous fly bacteria only grew to pinprick-size overnight, allowing visual distinction of the fast-growing bacteria used for infection (data not shown). mRNA was isolated from individual flies homogenized in 600 µl RLT buffer using RNAeasy kit (Qiagen, Hilden, Germany). Following DNAse digestion with Turbo DNA-free Kit (Ambion/Life Technologies, NY) RNA was reverse-transcribed with iScript cDNA synthesis kit (BioRad, CA) and gene expression was quantified by qRT-PCR using iQ SYBR Green Supermix (BioRad, CA).

Generation of an Iafgp-Expressing Mouse Line.

Iafgp was constitutively expressed under control of the chicken β-actin promoter in an iafgp-transgenic mouse line. The promoter region was excised from pβAct-CAT 9 (ATCC, VA) using XhoI and HindIII and subcloned into the pEGFP-1 vector (Clontech, CA). EGFP was removed from pβAct-EGFP-1 by digestion with BamHI and NotI resulting in pβAct-1. Iafgp was then PCR-amplified using oligomers iafgp BamHI F and iafgp NotI R, introducing the corresponding restriction sites. The PCR fragment was digested and cloned into linearized pβAct-1, resulting in pβAct-iafgp. For microinjection, the transgene fragment containing the β-actin promoter and iafgp gene was excised from pβAct-iafgp by digestion with XhoI and AflII restriction enzymes and gel purified. Microinjection was performed in 4-5 week old hybrid mouse embryos (C57BL/6×C3H) and mice were genotyped by PCR analysis of tail biopsies using IAFP4qRTF and IAFP4qRTR. mRNA expression of iafgp was confirmed in multiple tissues using the same primers for qRT-PCR. Transgenic iafgp-expressing mice were backcrossed for 8 generations to C57Bl/6 mice (Charles River, Mass.). Heterozygous experimental mice of 6-12 weeks were age- and sex-matched with wild-type littermates and wild-type C57Bl/6 as control. All mice were housed at 20-22° C. with water and food ad libitum. Animal handling was performed according to protocols approved by the Yale animal care and use committee.

Murine Challenges with Bacteria and Surgeries.

Cecal ligation and puncture surgery was performed as described[26,41]. Mice were anesthesized using isoflurane inhalation and the cecum was exteriorized through a peritoneal midline incision. Seventy-five percent of the cecum was ligated and punctured through and through with a 21 G hypodermic needle. A small amount of fecal material was squeezed out and the cecum was reinserted into the peritoneal cavity. After closing the abdomen in two layers mice received 1 ml saline subcutaneously. Buprenorphine was injected every 12 h for analgesia. Sham surgeries including cecal exteriorization but without ligation and puncture were performed as control. Survival and disease score (from healthy/alert, via slightly lethargic [slightly delayed response to experimenter, slowed movement] and lethargic [significantly reduced response to experimenter, raised fur, slowed and reduced movement] to very lethargic [body shaking, hunchback, absence of evasion movements] and dead) were monitored several times daily. Body surface temperature was measured dorsally using an infrared thermometer. A retro-orbital blood sample was taken daily and the cytokine levels of TNF-α, IL-6, IL12b and MCP-1 were measured using enzyme-linked immunosorbent assay (ELISA) kits (eBiosciences, San Diego, Calif.). Murine catheter implant surgery was performed as described[38]. Mice were anesthesized using isoflurane inhalation and a dorsal area was shaved. Following surface disinfection, a small incision was made on each mouse flank. Using a blunt probe a subcutanous pocket was formed and 2 cm catheter material (Vialon™ DB Biosciences, NJ) was inserted into each incision. Incisions were closed using suture and approximately 5×10⁶ CFU of exponentially growing *S. aureus* SA113 were injected through the skin into the lumen of the catheters. Three days post implant the devices were removed, rinsed once and then sonicated in PBS. The number of attached bacteria was determined by plating serial dilutions on agar plates.

Iafgp-expressing mice were infected with USA300 JE2. 1.2×108 CFU logarithmic growth phase bacteria per mouse were applied intranasally in 50 μl PBS and murine survival was monitored.

Statistical Analysis.

All experiments were repeated independently at least 3 times, if not noted otherwise. One representative experiment or pooled data are shown. Statistical differences between groups were analyzed using Students T-Test, One-Way ANOVA or Two-Way ANOVA with Tukey's or Sidak post-test. Differences in survival were calculated using the Log-rank (Mantel-Cox) or Gehan-Breslow-Wilcoxon test. P values below 0.05 were considered significant and marked with one asterisk, p<0.01 was marked with two asterisks and p<0.001 was marked with three asterisks. Calculations were performed using Excel 2007 (Microsoft, WA), survival analysis, graphing, and statistics were performed using Prism 6.0 software (GraphPad Software Inc, CA). CFU data were logarithmically transformed before statistical analysis.

EXAMPLES

In order that the invention described herein may be more fully understood, the following examples are set forth. It should be understood that these examples are for illustrative purposes only and are not to be construed to be limiting this invention in any manner.

Example 1: In Vitro Activity of IAFGP

Figure 1B:
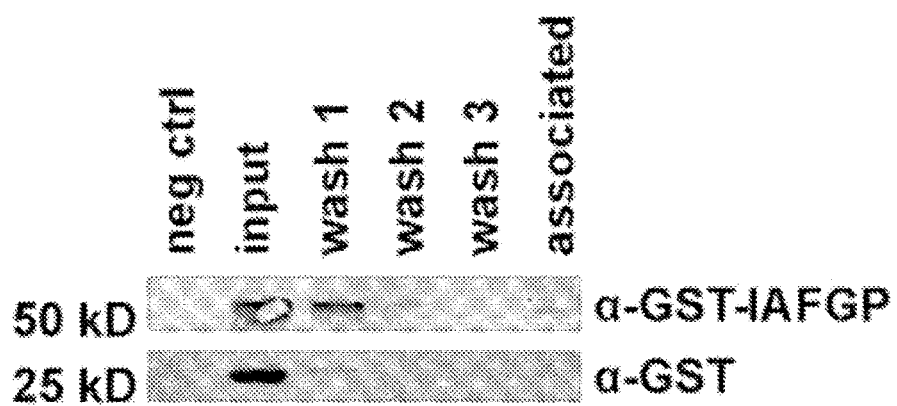
Figure 1C:
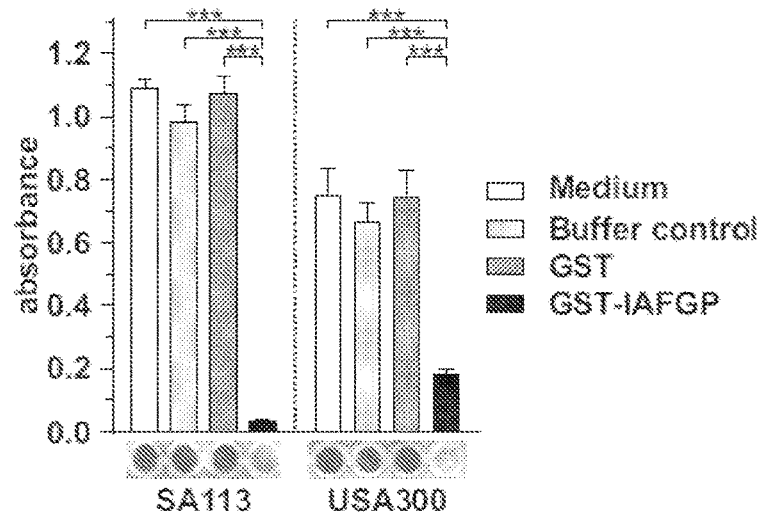
Figure 1D:
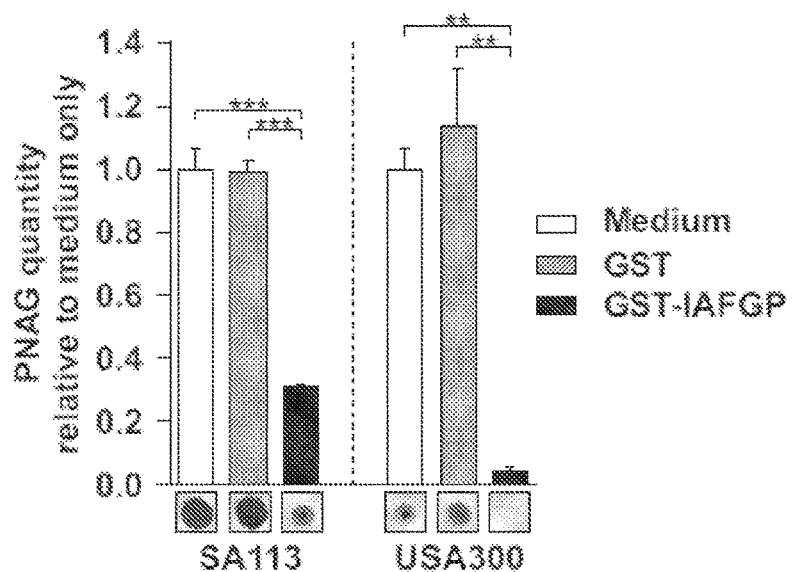
Figure 6:
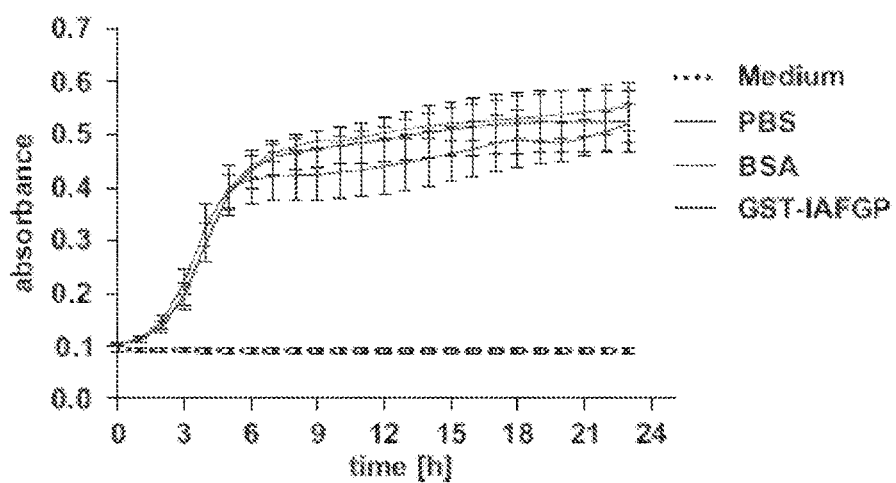
FIG. 6 shows that growth of *S. aureus* was unaffected by exposure to recombinant IAFGP-GST. A stationary culture of *S. aureus* was diluted to $OD_{600}=0.01$ in BHI medium and supplemented with 0.2 mg/ml recombinant IAFGP-GST, BSA or PBS as control. Bacterial growth was measured over time at $OD_{600}$ using a spectrophotometer. Growth curves from 5 independent experiments were pooled ±SEM. The bacterial growth curves indicate that recombinant IAFGP does not alter *S. aureus* growth in vitro.

IAFGP contributes to *L. scapularis* resistance against cold stress (Neelakanta et al. (2010) *J Clin Invest*). Described herein is an assessment of whether IAFGP is also involved in the host-pathogen response. Recombinant glutathione S-transferase (GST)-tagged IAFGP, but not GST alone, bound to the cell wall of various bacteria, as shown by immunoblot (FIG. 1A). Purified peptidoglycan was sufficient for IAFGP binding (FIG. 1B). In vitro, the addition of GST-IAFGP did not alter planktonic growth of the microbes; however, it strongly interfered with biofilm formation in static *S. aureus* cultures (FIG. 1C and FIG. 6). While mock- or GST-treated bacteria established a biofilm in glucose-supplemented medium, GST-IAFGP-treated microorganisms showed significantly reduced biofilm formation (FIG. 1C; p<0.001). Immunoblot data demonstrated decreased amounts of the exopolysaccharide poly-N-acetylglucosamine (PNAG), a major biofilm component, in bacteria exposed to GST-IAFGP (FIG. 1D; p<0.001). Similar to a prototypic *S. aureus* strain (SA113), methicillin-resistant *S. aureus* (MRSA) isolate (USA300), which are important drug-resistant organisms that cause substantial clinical disease, also bound GST-IAFGP, resulting in biofilm and PNAG suppression (FIGS. 1A, 1C, 1D; p<0.001 and p<0.01).

Figure 2A:
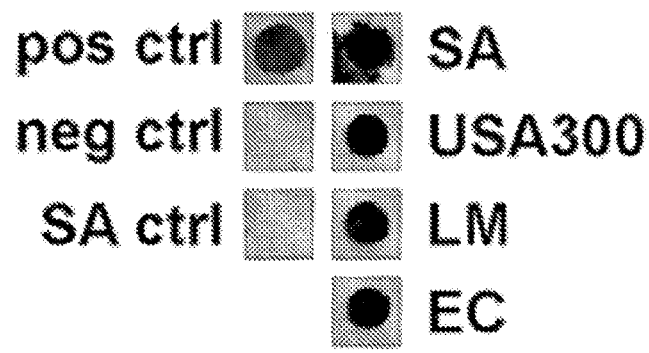
FIGS. 2A-2E show that binding of IAFGP peptide P1 to *S. aureus* interferes with biofilm formation in vitro.
Figure 2B:
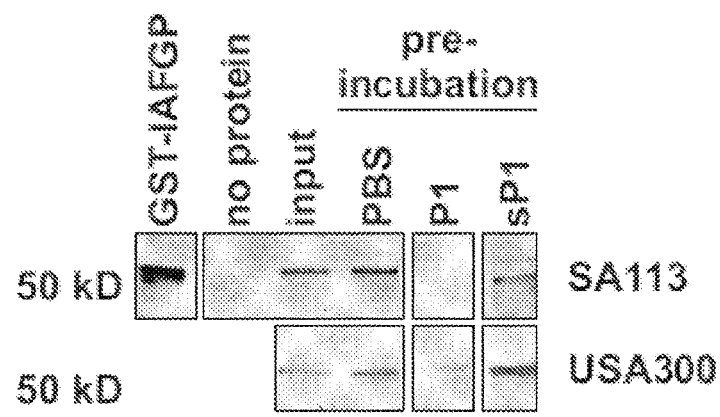
Figure 2C:
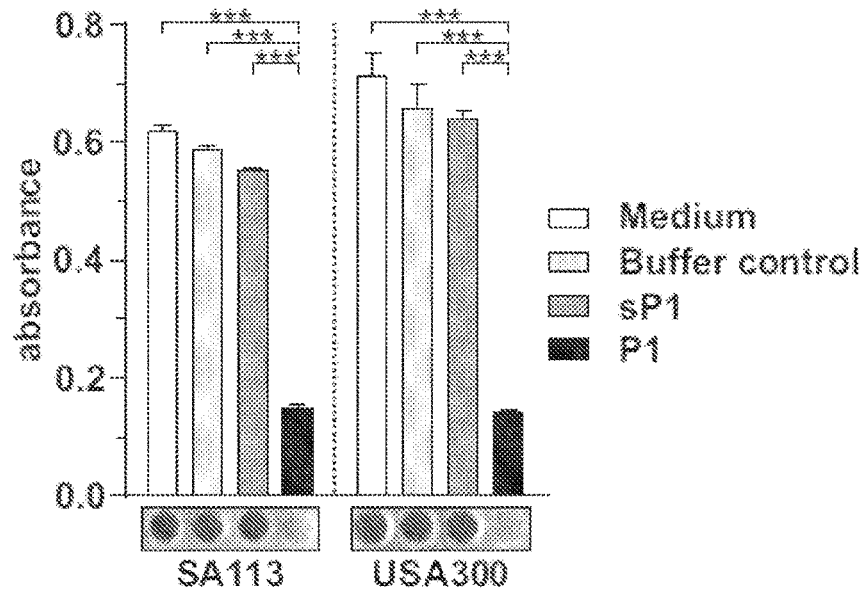
Figure 2D:
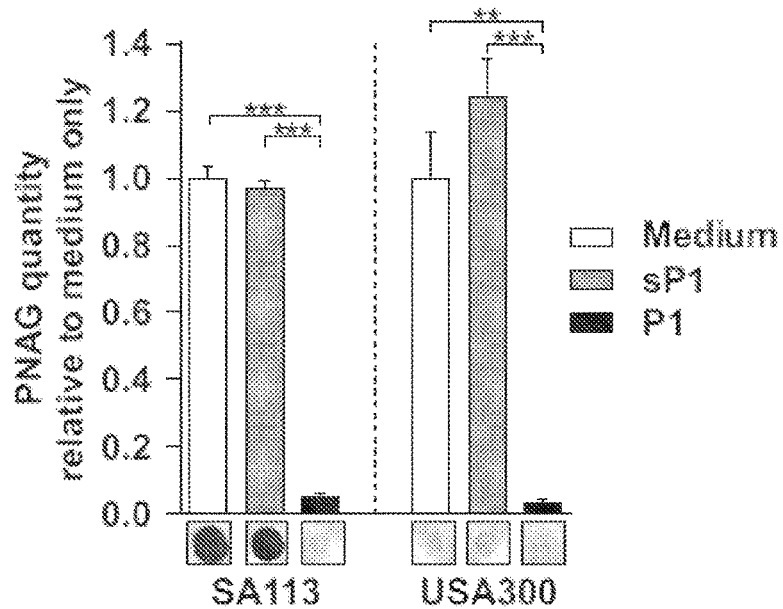
Figure 2E:
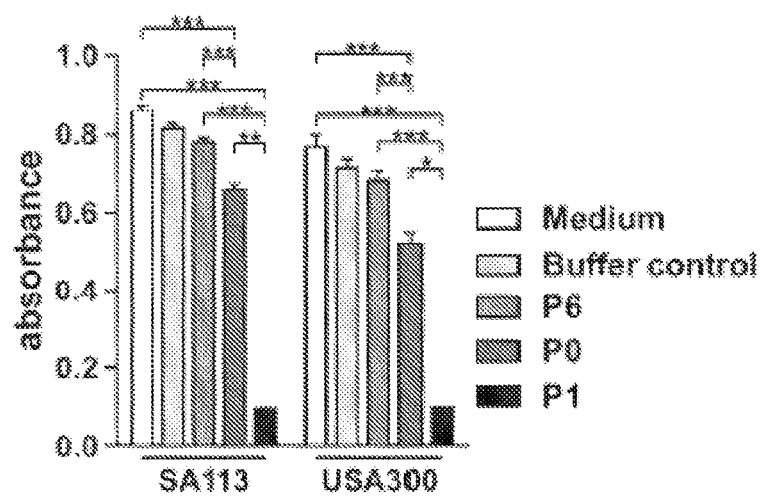
Figure 8:
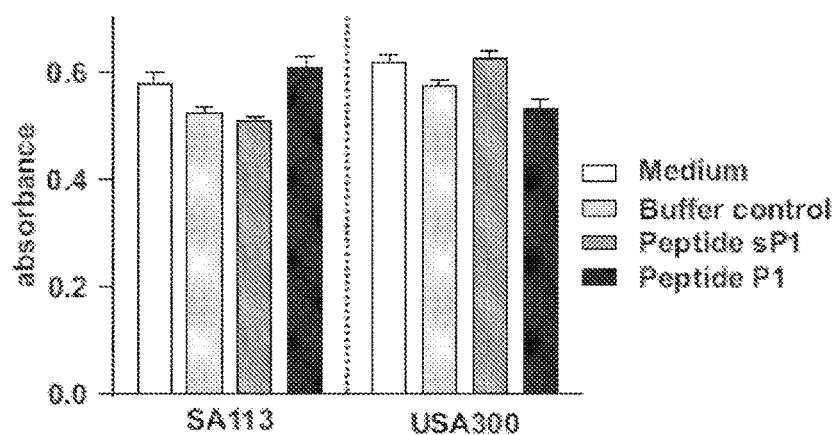
FIG. 8 shows that reduction of S. aureus biofilm formation by IAFGP or P1 does not influence bacterial growth. A stationary culture of S. aureus SA113 or USA300 JE2 was diluted in BHI/G to $OD_{600}$=0.01 supplemented with 0.1 mg/ml IAFGP-GST, GST, P1, sP1 or media alone. Following static incubation at 37° C. for 24 h bacterial density was measured at $OD_{600}$ using a spectrophotometer. Neither proteins nor peptides affected bacterial growth in vitro.

The vast majority of the primary amino acid sequence of IAFGP contains highly conserved peptide repeats. Except for the predicted N-terminal secretion signal, IAFGP is composed of repeats consisting of the canonical antifreeze glycoprotein (AFGP) amino acid triplets Ala-Ala-Thr (AAT) and Pro-Ala-Thr (PAT) interspersed between a 6 amino acid spacer sequence Pro-Ala-Arg-Lys-Ala-Arg (PARKAR, SEQ ID NO: 30), approximately every 21 amino acids (FIG. 7A). Eight of the 10 IAFGP repeats share a high level of identity, and the other 2 show variations in the spacer sequence. It was hypothesized that individual repeats might be involved in antimicrobial activity. A peptide (P1; PARKARA-ATAATAATAATAATAAT; SEQ ID NO: 1) with hallmarks of this domain, including a PARKAR (SEQ ID NO: 30) spacer followed by 6 AAT triplets, was synthesized to investigate this region's binding affinity for bacteria and antimicrobial activity (FIG. 7B). *S. aureus* was chosen as a model because it is a gram-positive organism of great clinical importance. Studies were extended to *Listeria* (*Listeria monocytogenes*), *Pseudomonas* (*Pseudomonas entomophila*), *Escherichia* (*Escherichia coli*) and *Serratia* (*Serratia marcescens*), to include an additional gram-positive agent and gram-negative microbes. P1 bound to different bacterial species (FIG. 2A). Peptide binding effectively competed with IAFGP for binding to the microbes, while scrambled P1 (sP1, SEQ ID NO: 5) served as a control (FIG. 2B). Similar to the full-length protein, P1 abrogated *S. aureus* biofilm formation and PNAG production under static culture conditions, but did not influence bacterial viability (FIGS. 2C, 2D, and 8; p<0.001 and p<0.001). These data demonstrate that IAFGP and P1 directly bind gram-positive and gram-negative pathogens and have capacity as anti-biofilm reagents.

Figure 3A:
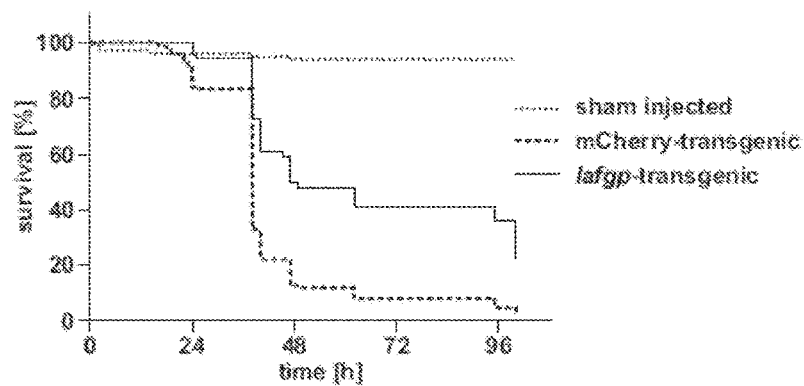
FIGS. 3A-3E present transgenic expression of iafgp in fruit flies and susceptibility of transgenic flies to *S. aureus* challenge in vivo.
Figure 3B:
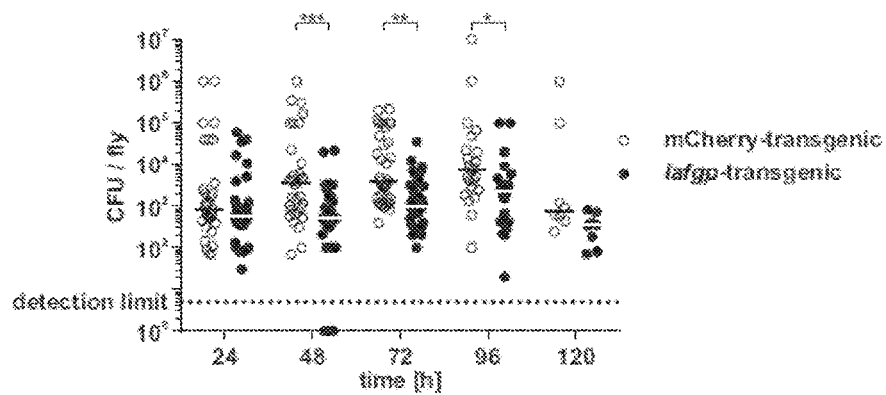
Figure 9A:
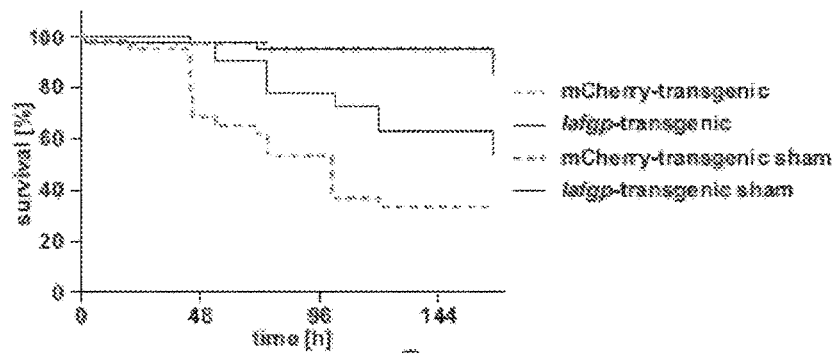
FIGS. 9A-9C show that iafgp-transgenic fruit flies show increased resistance to different bacterial pathogens.
Figure 9B:
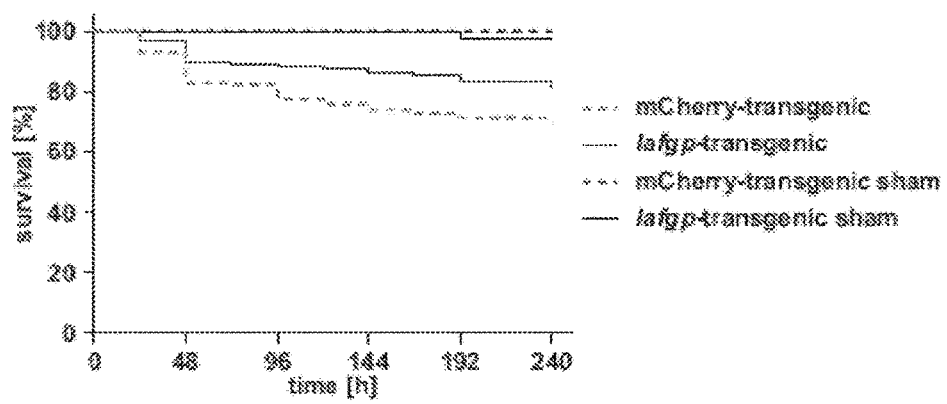
Figure 9C:
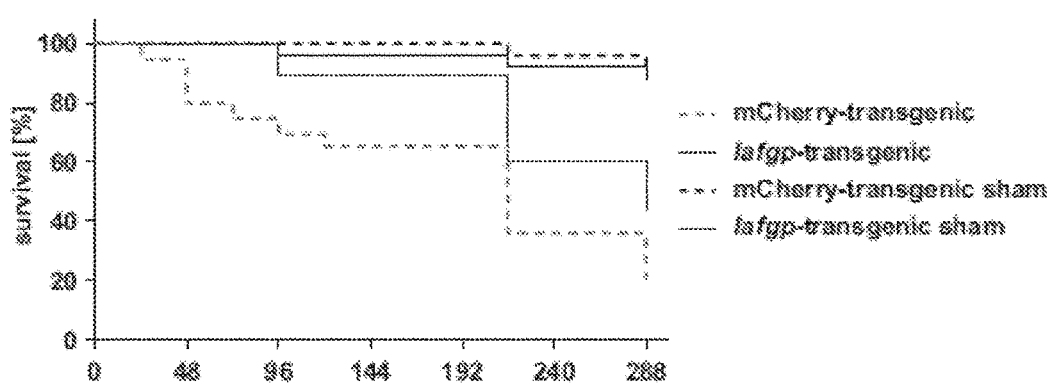

Example 2: Iafgp-Expressing *Drosophila melanogaster* Show Resistance Against Bacterial Infection Iafgp-expressing *D. melanogaster* (Neelakanta et al. (2012) *PLoS One* 7) were used to study the anti-infective activity of IAFGP in invertebrates. Fly infection by microinjection with *S. aureus* showed enhanced survival in comparison to controls (FIG. 3A; p<0.001). Needle prick infection with *Listeria monocytogenes* or oral infection with *Serratia marcescens* or *Pseudomonas entomophila* also showed increased fly survival, indicating a broad spectrum of protection using other established microbial infection methods (FIGS. 9A-9C; p<0.005, p<0.001, p<0.001). To discriminate between tolerance or resistance mechanisms causing the increase in survival, the pathogen load was quantified. The bacterial burden in control flies increased for 4 days, demonstrating microbial growth followed by host-mediated clearance. In contrast, the pathogen titers in iafgp-expressing flies remained stable over the course of infection indicating either reduced replication or growth homeostasis with host-induced killing (FIG. 3B). Bacterial titers in transgenic and control flies showed significant differences 2-4 days after challenge, suggesting that IAFGP is involved in infection resistance (FIG. 3B; p<0.001, p<0.01 and p<0.05).

Figure 3C:
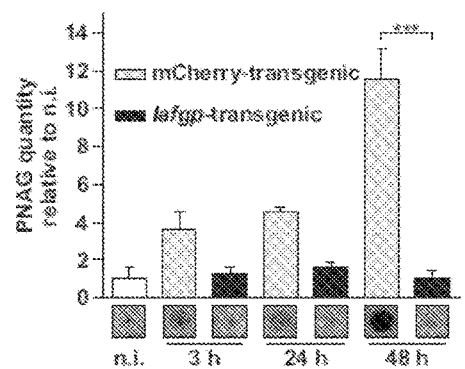
Figure 3D:
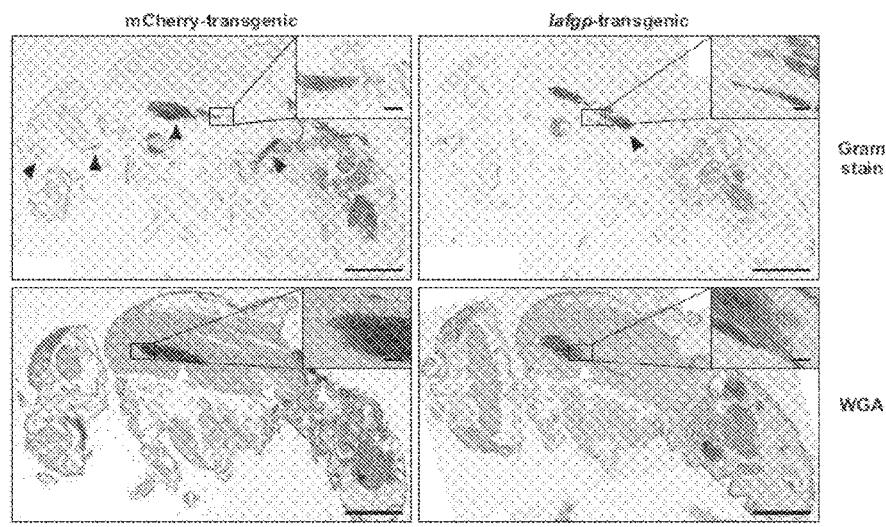
Figure 3E:
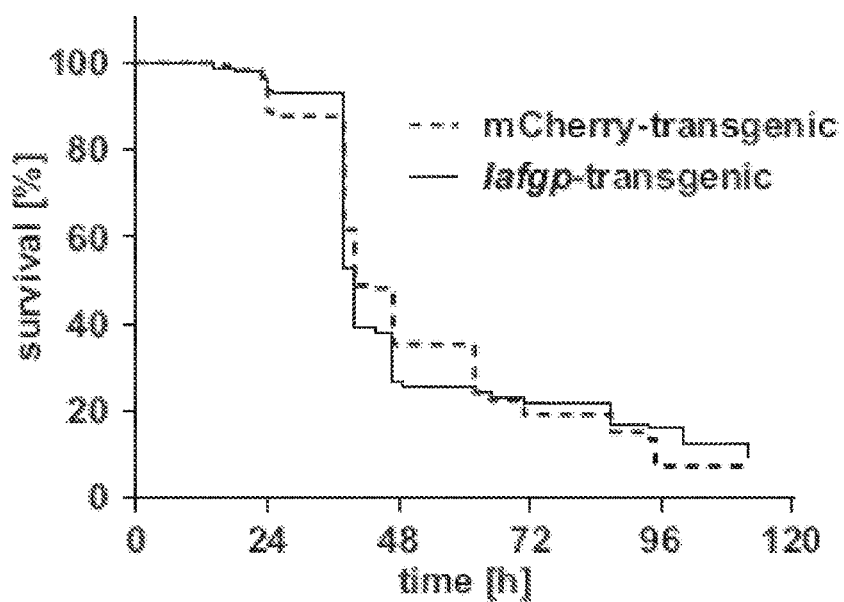
Figure 10:
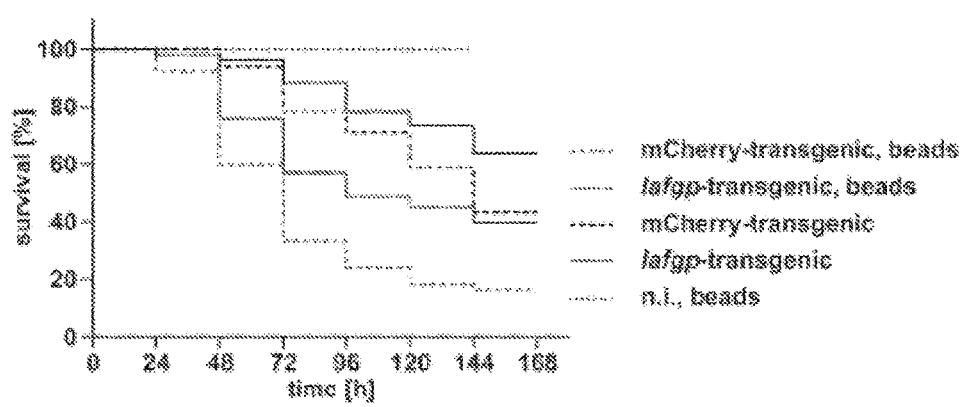
FIG. 10 shows that blocking phagocytosis in fruit flies does not abrogate the anti-infective function of IAFGP. Female 5-9 day old iafgp-expressing or control fruit flies were microinjected with 100 nl of 0.2 nm latex beads (Life technologies, NY) to block hemocyte phagocytosis. 3 h later the flies were challenged by microinjection of S. aureus SA113. The bacterial culture in stationary growth phase was diluted to $OD_{600}$=0.01, corresponding to 50-100 CFU per 9.2 nl inoculum. Fly survival was monitored over time. Data were pooled from 2 independent experiments (Log-rank test; p<0.001).
Figure 11:
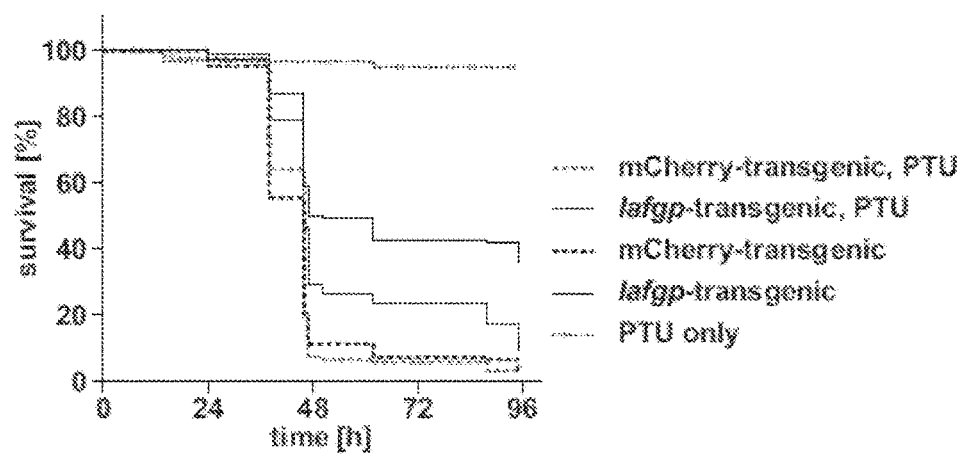
FIG. 11 shows that blocking melanization in fruit flies does not abrogate the anti-infective function of IAFGP. Female 5-9 day old iafgp-expressing or control fruit flies were microinjected with S. aureus SA113 resuspended in 10 mM N-Phenylthiourea (PTU) to block fly melanization. The bacterial culture in stationary growth phase was diluted to $OD_{600}$=0.1, corresponding to 500-1000 CFU per 9.2 nl inoculum. Survival was monitored over time. Data were pooled from 2 independent experiments (Log-rank test; p<0.001).
Figure 12A:
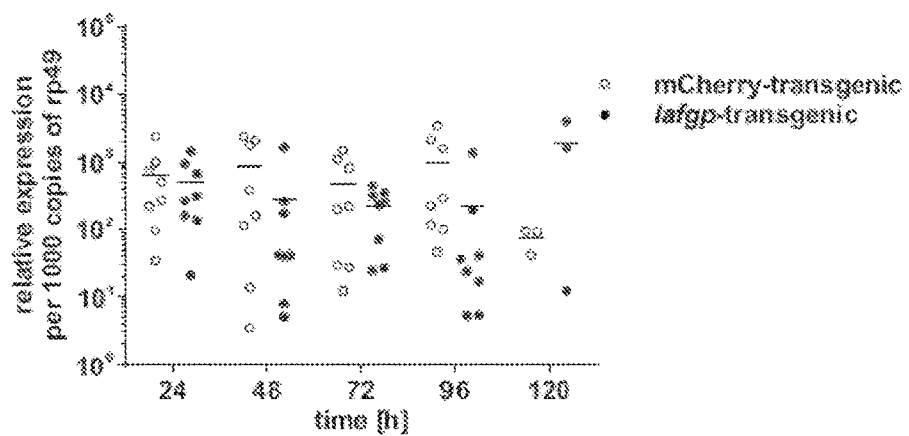
FIGS. 12A-12B show that mRNA expression of antimicrobial peptides is independent of IAFGP. Female 5-9 day old iafgp-expressing or control fruit flies were microinjected with S. aureus SA113. The bacterial culture in stationary growth phase was diluted to $OD_{600}$=0.01, corresponding to 50-100 CFU per 9.2 nl inoculum. Every 24 h the RNA of individual flies was isolated using the RNAeasy kit (Qiagen, Hilden, Germany), reverse transcribed with iScript cDNA synthesis kit (BioRad, CA) and gene expression was quantified by qRT-PCR using iQ SYBR Green Supermix (BioRad, CA).
Figure 12B:
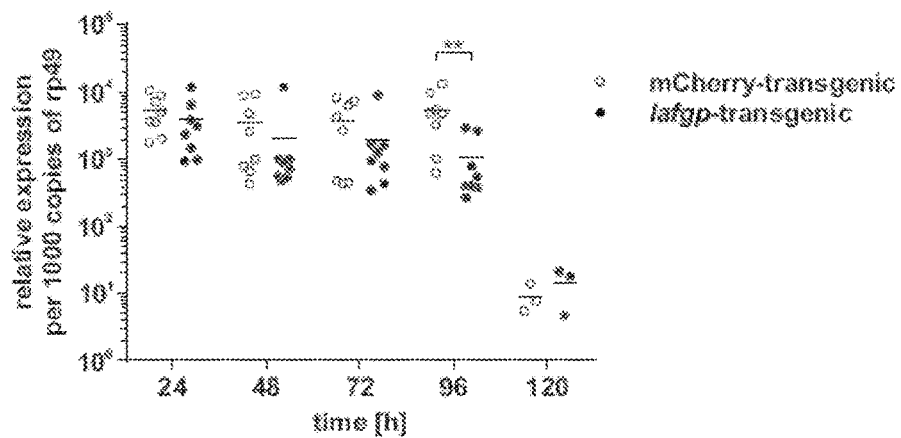

It was also assessed whether increased resistance of iafgp-expressing flies to *S. aureus* was due to a more efficient host response to infection or a direct effect on the bacteria. Fly immunity is comprised of three innate effector mechanisms. Hemocytes engulf pathogens similar to macrophages, antimicrobial peptides (AMPs) exert direct toxic effects, and melanin deposition leads to microbe encapsulation (Kim et al. (2005). *J Biochem Mol Biol*). All effector mechanisms contribute to the response against *S. aureus* challenge. Blocking fly phagocytosis or melanization during *S. aureus* infection affected survival of iafgp-expressing and control flies to a similar extent (FIGS. 10 and 11; p<0.001 latex bead injection, p<0.001 melantization inhibition) and AMP expression levels were not increased in iafgp-transgenic flies (FIG. 12, non-significant, p<0.01), suggesting that the anti-infective function of IAFGP is independent of fly immunity. In contrast, the PNAG quantity during *S. aureus* infection was reduced in iafgp-expressing flies compared to controls, consistent with the in vitro observations (FIG. 3C; p<0.001). Immunohistochemical detection of *S. aureus* and PNAG in infected flies confirmed the diminished bacterial colonization and the decrease in PNAG (FIG. 3D). When flies were challenged with a PNAG-deficient *S. aureus* ΔicaADBC mutant, the effect of IAFGP was completely abrogated (FIG. 3E). These data show that the anti-infective function of IAFGP in flies correlates with bacterial PNAG synthesis.

Figure 4A:
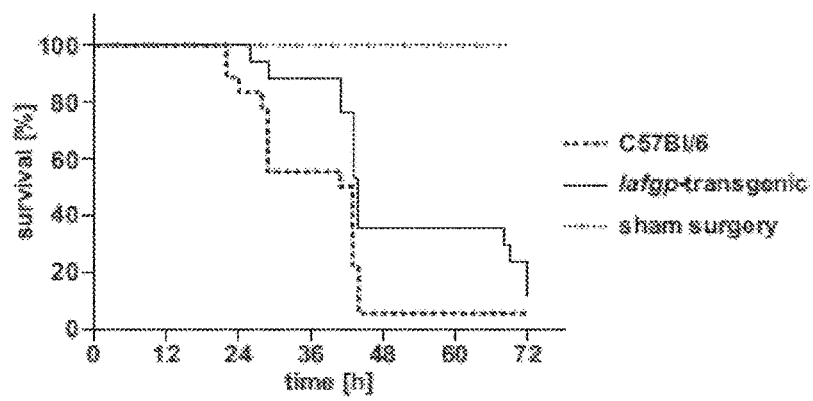
FIGS. 4A-4E present susceptibility of iafgp-expressing mice to polymicrobial sepsis or *S. aureus* USA300 challenge.
Figure 4B:
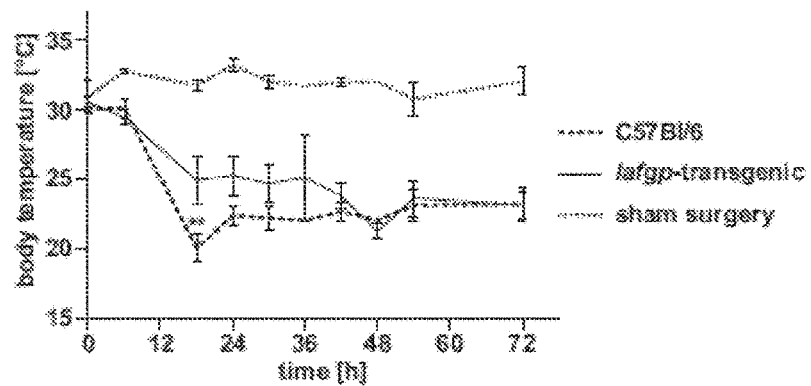
Figure 4C:
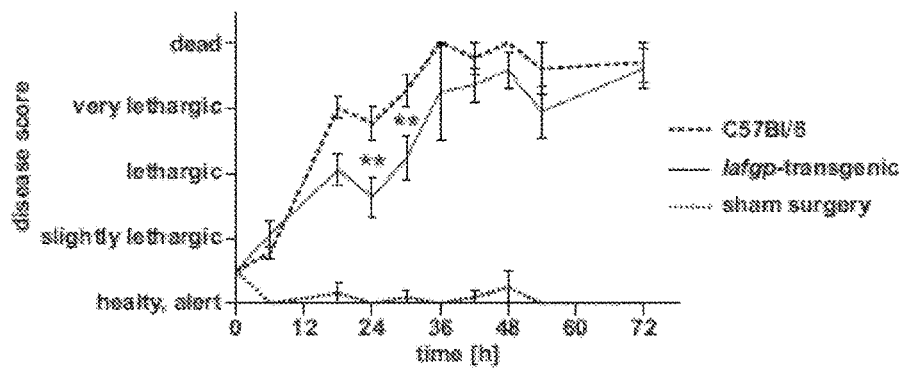
Figure 4D:
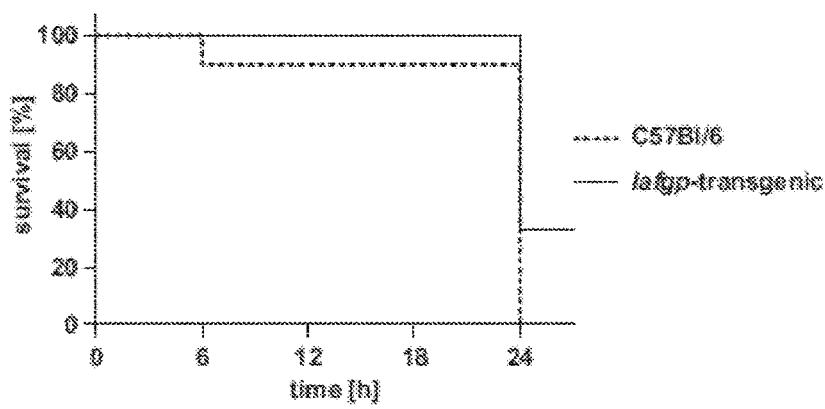
Figure 4E:
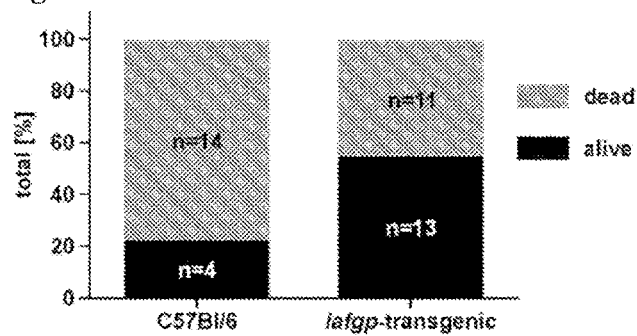
Figure 13:
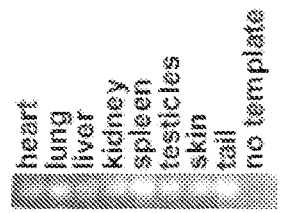
FIG. 13 shows that iafgp-transgenic mice have transgene expression in all examined organs. Homozygous iafgp-transgenic mice, backcrossed for 8 generations to C57Bl/6, were sacrificed and various tissues were harvested. RNA was isolated using the RNAeasy kit (Qiagen, Hilden, Germany), reverse transcribed with iScript cDNA synthesis kit (BioRad, CA), and gene expression was detected by RT-PCR using iQ SYBR Green Supermix (BioRad, CA) followed by size separation using agarose gel electrophoresis.
Figure 14A:
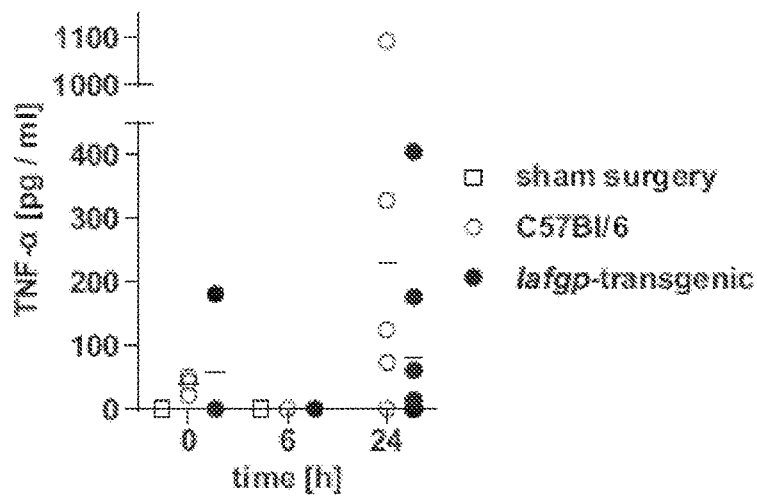
FIGS. 14A-14D shows that following cecal ligation and puncture surgery, iafgp-transgenic mice have a delayed serum cytokine level response. Cecal ligation and puncture surgery was performed on iafgp-transgenic mice and controls as described. Mice were bled retro-orbitally only if the health status of the animals permitted; no samples were obtained later than 24 h post-surgery.
Figure 14B:
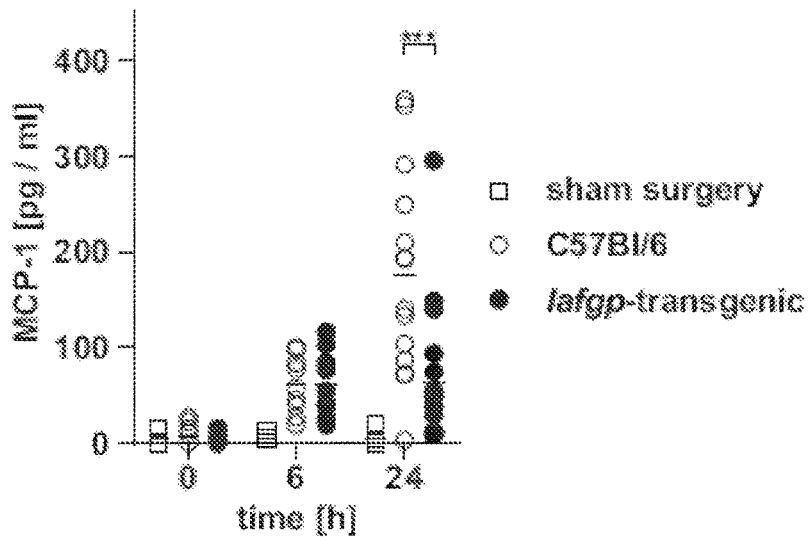
Figure 14C:
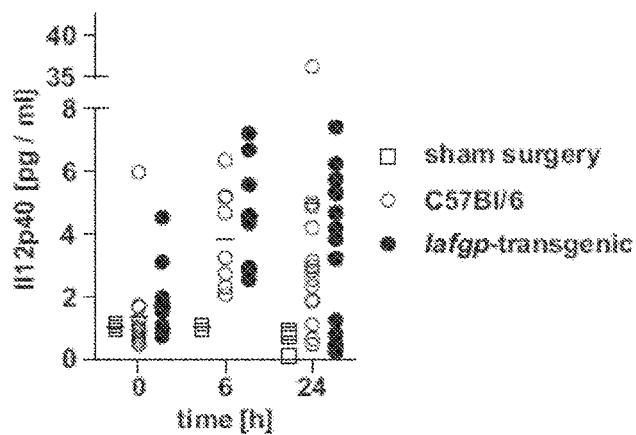
Figure 14D:
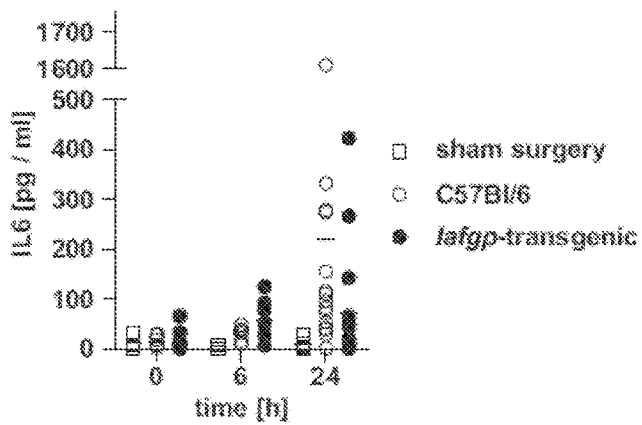

Example 3: Iafgp-Expressing Mice Show Increased Resistance to Bacterial Challenge and Sepsis As IAFGP shows anti-infective activity in vitro and in an invertebrate model of infection, the function of IAFGP was also assessed in vertebrates. A transgenic mouse line expressing iafgp ubiquitously was produced (FIG. 13). Mice were subjected to cecal ligation and puncture (CLP), a well-characterized model of polymicrobial sepsis (Rittirsch et al. (2009) *Nat Protoc*). Results showed increased survival of iafgp-expressing mice in comparison to controls after CLP surgery (p<0.05), reflected by a 35% extended average survival (FIG. 4A). Hypothermia and serum cytokine release of MCP-1, TNF-α, IL6 and IL12p40, characteristic traits of sepsis, were delayed in iafgp-expressing mice compared to control animals (FIG. 4B, p<0.001; FIG. 14). The transgenic animals also recorded significantly better general health and activity at 24-36 h after surgery than control mice (p<0.05, FIG. 4C). A monomicrobial intranasal challenge with MRSA also demonstrated enhanced survival of iafgp-transgenic mice compared to controls (FIGS. 4D and 4E; p<0.05). Collectively, these results show that IAFGP affords protection for mice against bacterial infection.

Example 4: Coating of Catheter Biomaterial with P1 Prevents Biofilm Formation

Figure 5A:
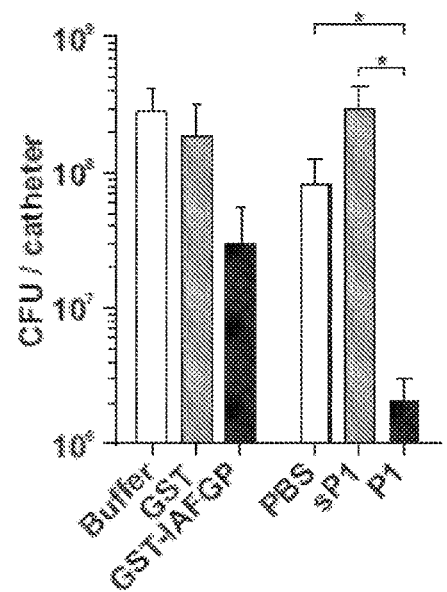
FIGS. 5A-5C show that P1 associates with intravenous catheters and restricts *S. aureus* biofilm formation in vitro and in vivo.
Figure 5B:
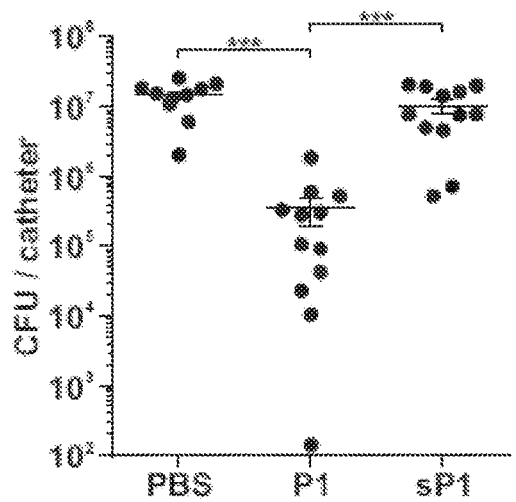
Figure 5C:
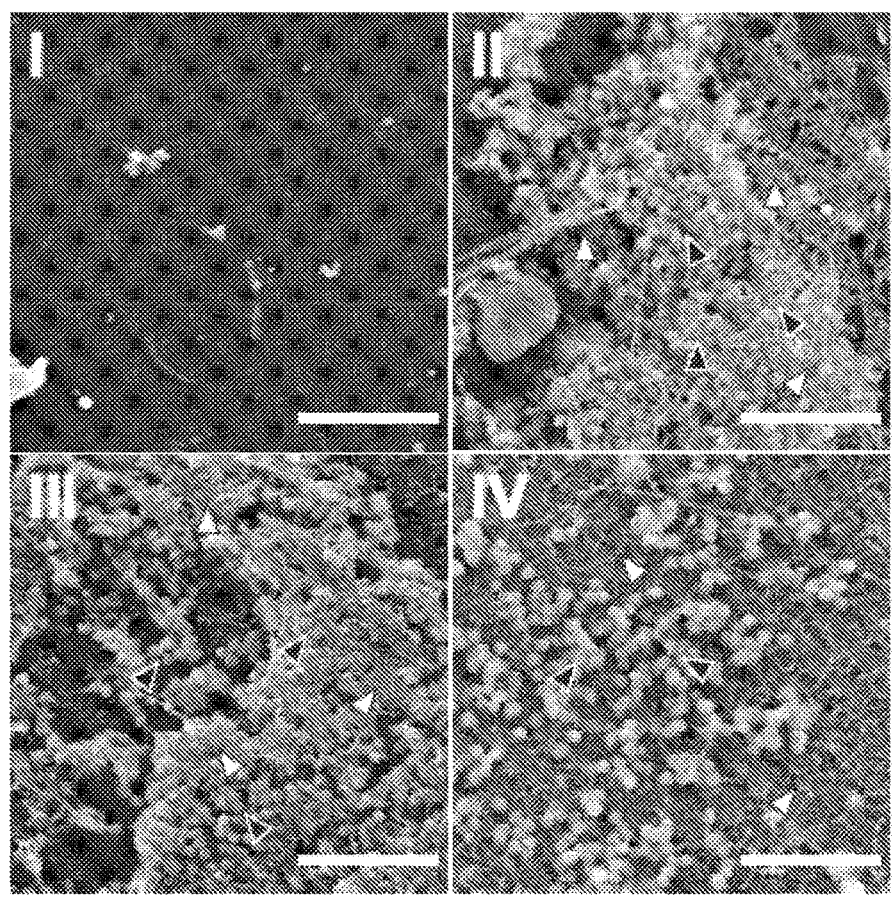

Staphylococci are responsible for half of the catheter-related bloodstream infections in the US (Maki et al. (2006) *Mayo Clinic Proceedings*; Raad et al. (2002) *Arch Intern Med*; Ramos et al. (2011) *Crit Care Med*). *S. aureus* alone accounts for 20% of these incidences and is associated with high morbidity and mortality (Walz et al. (2010) *Journal of Intensive Care Medicine*; Walz (2010) *J Intensive Care Med*). To investigate whether IAFGP or P1 interfere with bacterial attachment to biomaterials, intravenous catheters were incubated in protein or peptide solution and then transferred into *S. aureus* suspensions. IAFGP and P1 spontaneously associated with the catheters and reduced biofilm formation (FIG. 5A). Associated bacteria were lowered 9- and 40-fold, respectively, in comparison to untreated controls (FIG. 5A; p<0.05). To investigate biofilm formation in vivo, P1-coated catheters were implanted subcutaneously into mice and inoculated with *S. aureus*. 72 h later, the catheters were removed and examined for bacterial attachment and biofilm formation. P1-coated catheters demonstrated more than 40-fold reduction in the number of attached bacteria in comparison to mock-treated catheters (FIG. 5B, p<0.001). Scanning electron microscopy analysis of explanted catheters confirmed PNAG abrogation in *S. aureus* biofilms when catheters were coated with P1 (FIG. 5C). The reduced biofilm formation on biomaterials confirmed the in vivo activity of P1 and suggests its application as prophylactic coating to prevent bacterial attachment.

Figure 16:
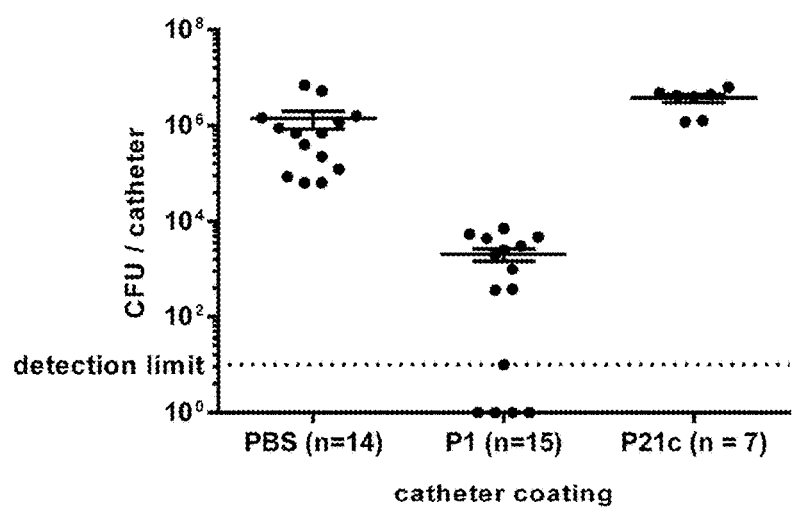
FIG. 16 shows bacterial attachment to intravenous catheters that had been incubated in PBS, P1 (SEQ ID NO: 1) or P21c (SEQ ID NO: 5) and implanted subcutaneously on the dorsal flanks of C57Bl/6 mice. Seven days after catheter inoculation with *S. aureus* SA113, the catheters were removed, and the attached bacteria were quantified by plating serial dilutions.

Similar experiments were performed in which P1- or P1c-coated catheters were implanted subcutaneously into mice and inoculated with *S. aureus*. After 7 days, the catheters were removed and assessed for bacterial attachment (FIG. 16). The catheters that had been coated with peptide P1 had a 600-fold reduction in the number of attached bacteria in comparison to PBS-treated catheters, with 4 of the 15 P1-coated catheters having no attached bacteria and 1 with 1 detectable colony forming unit. These data indicate that the peptide coating is sufficient to reduce *S. aureus* biofilm formation to a level that may be low enough for eradication by the host immune system. Even in the absence of additional antimicrobial treatment, the P1 peptide abrogates bacteria in approximately 30% of cases.

Several peptides with native or modified sequences of the tick antifreeze protein IAFGP have been assessed. Peptide P2 (renamed and referred to herein as peptide P1) has been shown to act as an anti-infective, as described herein. Other peptides containing part of the IAFGP sequence have been developed and are being tested for activity. Preliminary data show that anti-biofilm activity has been identified with peptide P0, which includes one native repeat of IAFGP. Peptides P6 and P21c were used as negative controls.

Below is the amino acid sequence of IAFGP and a list of screened peptides.

IAFGP amino acid sequence (SEQ ID NO: 3):

| 1 | MTTLLRLTILIVAVAGVLGSSKRAAR |
|---|---|
| 27 | AATPATAATPATPATAAT |
| 45 | PAI AATPATAATPATAAT |
| 63 | PARKAR AATPATPATPATAATPATAAT |
| 90 | PARKAR AATAATPATPATAAT |
| 111 | PARKAR AATPATPATAATPATAAT |
| 135 | PARKAR AATPATPATAATPATAAT |
| 159 | PARKAR AATPATPATAATPATAAT |
| 183 | PARKAR AATPATPATAATAAT |
| 204 | PARKAR AATAATPATPATAAT |
| 225 | PARKAR AATPATAATAATPATAATAAA |

Examined peptides:

P0 (native IAFGP sequence aa 111-134): PARKARAATPATPATAATPATAAT (SEQ ID NO.: 2)

P1 ('AAT' triplets of P0 replaced by 'PAT' triplets): PARKARPATPATPATPATPATPAT (SEQ ID NO:20); not referred to herein as P1

P2 ('PAT' triplets of P0 replaced by 'AAT' triplets; P2 is labeled/referred to as P1 herein): PARKARAATAATAATAATAAT (SEQ ID NO.: 1)

P3 ('PARKAR' leader with double 'AAT/PAT' repeats): PARKARAATPATPATAATPATAATAATPATPATAATPATAAT (SEQ ID NO:21)

P4 ('AAT & PAT' triplets without 'PARKAR' leader): AATPATPATAATPATAAT (SEQ ID NO:22)

P5 ('PARKAR' in the middle of peptide): AATPATAATPARKARAATPATPAT (SEQ ID NO:23)

P6 (scrambled P0): TTPAPTKATARARAAPTAAATPAA (negative control) (SEQ ID NO:4)

P13 (P2 with four 'AAT' repeats): PARKARAATAATAATAAT (SEQ ID NO:24)

P14 (P2 with two 'AAT' repeats): PARKARAATAAT (SEQ ID NO:25)

P15 (two 'AAT', 'PARKAR', two 'AAT'): AATAATPARKARAATAAT (SEQ ID NO:26)

P16 (six 'AAT' triplets without 'PARKAR'): AATAATAATAATAATAAT (SEQ ID NO:27)

P22 (Quadruple PARKAR): PARKARPARKARPARKARPARKAR (SEQ ID NO:28)

P23 (P2 with 8 'AAT' triplets): PARKARAATAATAATAATAATAATAATAAT (SEQ ID NO:29)

P21c (P2 randomized, soluble, used as control for several assays, P21c is labeled/referred to as sP1 herein): AAAAATATAAARRAAAAPTTAKTT (negative control) (SEQ ID NO:5)

REFERENCES

1 Clark, M. S. & Worland, M. R. How insects survive the cold: molecular mechanisms—a review. *J Comp Physiol B* 178, 917-933, doi:10.1007/s00360-008-0286-4 (2008).

2 Davies, P. L. & Sykes, B. D. Antifreeze proteins. *Curr Opin Struct Biol* 7, 828-834, doi:S0959-440X(97) 80154-6 [pii] (1997).

3 Doucet, D., Walker, V. K. & Qin, W. The bugs that came in from the cold: molecular adaptations to low temperatures in insects. *Cellular and molecular life sciences: CMLS* 66, 1404-1418, doi:10.1007/s00018-009-8320-6 (2009).

4 Harding, M. M., Anderberg, P. I. & Haymet, A. D. 'Antifreeze' glycoproteins from polar fish. *European journal of biochemistry/FEBS* 270, 1381-1392 (2003).

5 Sharp, K. A. A peek at ice binding by antifreeze proteins. *Proceedings of the National Academy of Sciences of the United States of America* 108, 7281-7282, doi:10.1073/pnas.1104618108 (2011).

6 Venketesh, S. & Dayananda, C. Properties, potentials, and prospects of antifreeze proteins. *Critical Reviews in Biotechnology* 28, 57-82, doi:10.1080/07388550801891152 (2008).

7 Carvajal-Rondanelli, P. A., Marshall, S. H. & Guzman, F. Antifreeze glycoprotein agents: structural requirements for activity. *J Sci Food Agric* 91, 2507-2510, doi:10.1002/jsfa.4473 (2011).

8 Garner, J. & Harding, M. M. Design and synthesis of antifreeze glycoproteins and mimics. *Chembiochem: a European journal of chemical biology* 11, 2489-2498, doi:10.1002/cbic.201000509 (2010).

9 Peltier, R. et al. Synthesis and antifreeze activity of fish antifreeze glycoproteins and their analogues. *Chemical Science* 1, 538-551, doi:10.1039/c0sc00194e (2010).

10 Brownstein, J. S., Holford, T. R. & Fish, D. A climate-based model predicts the spatial distribution of the Lyme disease vector *Ixodes scapularis* in the United States. *Environ Health Perspect* 111, 1152-1157 (2003).

11 Yuval, B. & Spielman, A. Duration and regulation of the developmental cycle of *Ixodes dammini* (Acari: Ixodidae). *J Med Entomol* 27, 196-201 (1990).

12 Neelakanta, G., Sultana, H., Fish, D., Anderson, J. F. & Fikrig, E. *Anaplasma phagocytophilum* induces *Ixodes scapularis* ticks to express an antifreeze glycoprotein gene that enhances their survival in the cold. *J Clin Invest* 120, 3179-3190, doi:42868 [pii] 10.1172/JCI42868 (2010).

13 Neelakanta, G., Hudson, A. M., Sultana, H., Cooley, L. & Fikrig, E. Expression of *Ixodes scapularis* antifreeze glycoprotein enhances cold tolerance in *Drosophila melanogaster*. *PLoS One* 7, e33447, doi:10.1371/journal.pone.0033447 (2012).

14 Griffith, M. & Yaish, M. W. Antifreeze proteins in overwintering plants: a tale of two activities. *Trends Plant Sci* 9, 399-405, doi:10.1016/j.tplants.2004.06.007 (2004).

15 Hon, W. C., Griffith, M., Chong, P. & Yang, D. Extraction and Isolation of Antifreeze Proteins from Winter Rye (*Secale cereale* L.) Leaves. *Plant physiology* 104, 971-980 (1994).

16 Hon, W. C., Griffith, M., Mlynarz, A., Kwok, Y. C. & Yang, D. S. Antifreeze proteins in winter rye are similar to pathogenesis-related proteins. *Plant physiology* 109, 879-889 (1995).

17 Huang, T. & Duman, J. G. Cloning and characterization of a thermal hysteresis (antifreeze) protein with DNA-binding activity from winter bittersweet nightshade, *Solanum dulcamara*. *Plant molecular biology* 48, 339-350 (2002).

18 Meyer, K., Keil, M. & Naldrett, M. J. A leucine-rich repeat protein of carrot that exhibits antifreeze activity. *FEBS letters* 447, 171-178 (1999).

19 Smallwood, M. et al. Isolation and characterization of a novel antifreeze protein from carrot (*Daucus carota*). *The Biochemical journal* 340 (Pt 2), 385-391 (1999).

20 Yaish, M. W., Doxey, A. C., McConkey, B. J., Moffatt, B. A. & Griffith, M. Cold-active winter rye glucanases with ice-binding capacity. *Plant physiology* 141, 1459-1472, doi:10.1104/pp.106.081935 (2006).

21 Zhang, D. Q. et al. Carrot antifreeze protein does not exhibit the polygalacturonase-inhibiting activity of PGIP family. *Yi chuan xue bao=Acta genetica Sinica* 33, 1027-1036, doi:10.1016/S0379-4172(06)60139-X (2006).

22 Zhang, S., Wei, Y. & Pan, H. Transgenic rice plants expressing a novel antifreeze glycopeptide possess resistance to cold and disease. *Z Naturforsch C* 62, 583-591 (2007).

23 Chen, L., DeVries, A. L. & Cheng, C. H. Convergent evolution of antifreeze glycoproteins in Antarctic nototh-enioid fish and Arctic cod. *Proceedings of the National Academy of Sciences of the United States of America* 94, 3817-3822 (1997).

24 Fletcher, G. L., Hew, C. L. & Davies, P. L. Antifreeze proteins of teleost fishes. *Annual review of physiology* 63, 359-390, doi:10.1146/annurev.physiol.63.1.359 (2001).

25 Kim, T. & Kim, Y. J. Overview of innate immunity in *Drosophila*. *J Biochem Mol Biol* 38, 121-127 (2005).

26 Rittirsch, D., Huber-Lang, M. S., Flierl, M. A. & Ward, P. A. Immunodesign of experimental sepsis by cecal ligation and puncture. *Nat Protoc* 4, 31-36, doi:10.1038/nprot.2008.214 (2009).

27 Maki, D. G., Kluger, D. M. & Crnich, C. J. The Risk of Bloodstream Infection in Adults With Different Intravascular Devices: A Systematic Review of 200 Published Prospective Studies. *Mayo Clinic Proceedings* 81, 1159-1171, doi:dx.doi.org/10.4065/81.9.1159 (2006).

28 Raad, II & Hanna, H. A. Intravascular catheter-related infections: new horizons and recent advances. *Arch Intern Med* 162, 871-878 (2002).

29 Ramos, E. R. et al. Clinical effectiveness and risk of emerging resistance associated with prolonged use of antibiotic-impregnated catheters: more than 0.5 million catheter days and 7 years of clinical experience. *Crit Care Med* 39, 245-251, doi:10.1097/CCM.0b013e3181feb83e (2011).

30 Walz, J. M., Memtsoudis, S. G. & Heard, S. O. Analytic Reviews: Prevention of Central Venous Catheter Bloodstream Infections. *Journal of Intensive Care Medicine* 25, 131-138 (2010).

31 Walz, J. M., Memtsoudis, S. G. & Heard, S. O. Prevention of central venous catheter bloodstream infections. *J Intensive Care Med* 25, 131-138, doi:10.1177/0885066609358952 (2010).

32 Nishimura, S., Tsurumoto, T., Yonekura, A., Adachi, K. & Shindo, H. Antimicrobial susceptibility of *Staphylococcus aureus* and *Staphylococcus epidermidis* biofilms isolated from infected total hip arthroplasty cases. *J Orthop Sci* 11, 46-50, doi:10.1007/s00776-005-0968-7 (2006).

33 Vuong, C. et al. Polysaccharide intercellular adhesin (PIA) protects *Staphylococcus epidermidis* against major components of the human innate immune system. *Cell Microbiol* 6, 269-275 (2004).

34 Otto, M. Staphylococcal biofilms. *Curr Top Microbiol Immunol* 322, 207-228 (2008).

35 Cywes-Bentley, C. et al. Antibody to a conserved antigenic target is protective against diverse prokaryotic and eukaryotic pathogens. *Proc Natl Acad Sci USA* 110, E2209-2218, doi:10.1073/pnas.1303573110 (2013).

36 Bouma, H. R., Henning, R. H., Kroese, F. G. & Carey, H. V. Hibernation is associated with depression of T-cell independent humoral immune responses in the 13-lined ground squirrel. *Dev Comp Immunol* 39, 154-160, doi:10.1016/j.dci.2012.11.004 (2013).

37 Triggs, A. & Knell, R. J. Interactions between environmental variables determine immunity in the Indian meal moth *Plodia interpunctella*. *J Anim Ecol* 81, 386-394, doi:10.1111/j.1365-2656.2011.01920.x (2012).

38 Christensen, G. D. et al. Adherence of coagulase-negative staphylococci to plastic tissue culture plates: a quantitative model for the adherence of staphylococci to medical devices. *J Clin Microbiol* 22, 996-1006 (1985).

39 Bownes, M. et al. Drosophila: A Laboratory Handbook. By Michael Ashburner. New York: Cold Spring Harbor Laboratory. 1989. 1331 pages. Price $180.00. ISBN 0 87969 321 5. Drosophila: A Laboratory Manual. By Michael Ashburner. New York: Cold Spring Harbor Laboratory. 1989. 434 pages. Price $50.00. ISBN 0 97969 322 3.

40 Price for the set: $230.00. *Genet Res (Camb)* 56, 71-73 (1990). Apidianakis, Y. & Rahme, L. G. *Drosophila melanogaster* as a model host for studying *Pseudomonas aeruginosa* infection. *Nat Protoc* 4, 1285-1294, doi:10.1038/nprot.2009.124 (2009).

41 Silver, A. C., Arjona, A., Walker, W. E. & Fikrig, E. The circadian clock controls toll-like receptor 9-mediated innate and adaptive immunity. *Immunity* 36, 251-261, doi:10.1016/j.immuni.2011.12.017 (2012).

What is claimed is:

1. A method of reducing, partially or completely, microbial colonization of a surface of a medical device, comprising:
    coating onto or applying to the surface a composition comprising a peptide that is identical to the sequence of SEQ ID NO:1 (P1 sequence) or a peptide that is at least 95% identical to the sequence of SEQ ID NO:1.

2. The method of claim 1, wherein the medical device is a catheter.

3. The method of claim 1, wherein the microbial colonization is colonization by gram-positive pathogen, gram-negative pathogen or both gram-positive pathogen and gram-negative pathogen.

* * * * *

SEQUENCE LISTING

```
<160> NUMBER OF SEQ ID NOS: 32

<210> SEQ ID NO 1
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 1

Pro Ala Arg Lys Ala Arg Ala Ala Thr Ala Ala Thr Ala Ala Thr Ala
1               5                   10                  15

Ala Thr Ala Ala Thr Ala Ala Thr
            20

<210> SEQ ID NO 2
```

```
<211> LENGTH: 24
<212> TYPE: PRT
<213> ORGANISM: Ixodes scapularis

<400> SEQUENCE: 2

Pro Ala Arg Lys Ala Arg Ala Ala Thr Pro Ala Thr Pro Ala Thr Ala
1               5                   10                  15

Ala Thr Pro Ala Thr Ala Ala Thr
            20

<210> SEQ ID NO 3
<211> LENGTH: 251
<212> TYPE: PRT
<213> ORGANISM: Ixodes scapularis

<400> SEQUENCE: 3

Met Thr Thr Leu Leu Arg Leu Thr Ile Leu Ile Val Ala Val Ala Gly
1               5                   10                  15

Val Leu Gly Ser Ser Lys Arg Ala Ala Arg Ala Ala Thr Pro Ala Thr
            20                  25                  30

Ala Ala Thr Pro Ala Thr Pro Ala Thr Ala Ala Thr Pro Ala Ile Ala
        35                  40                  45

Ala Thr Pro Ala Thr Ala Ala Thr Pro Ala Thr Ala Ala Thr Pro Ala
    50                  55                  60

Arg Lys Ala Arg Ala Ala Thr Pro Ala Thr Pro Ala Thr Pro Ala Thr
65                  70                  75                  80

Ala Ala Thr Pro Ala Thr Ala Ala Thr Pro Ala Arg Lys Ala Arg Ala
                85                  90                  95

Ala Thr Ala Ala Thr Pro Ala Thr Pro Ala Thr Ala Ala Thr Pro Ala
            100                 105                 110

Arg Lys Ala Arg Ala Ala Thr Pro Ala Thr Pro Ala Thr Ala Ala Thr
        115                 120                 125

Pro Ala Thr Ala Ala Thr Pro Ala Arg Lys Ala Arg Ala Ala Thr Pro
    130                 135                 140

Ala Thr Pro Ala Thr Ala Ala Thr Pro Ala Thr Ala Ala Thr Pro Ala
145                 150                 155                 160

Arg Lys Ala Arg Ala Ala Thr Pro Ala Thr Pro Ala Thr Ala Ala Thr
                165                 170                 175

Pro Ala Thr Ala Ala Thr Pro Ala Arg Lys Ala Arg Ala Ala Thr Pro
            180                 185                 190

Ala Thr Pro Ala Thr Ala Ala Thr Ala Ala Thr Pro Ala Arg Lys Ala
        195                 200                 205

Arg Ala Ala Thr Ala Ala Thr Pro Ala Thr Pro Ala Thr Ala Ala Thr
    210                 215                 220

Pro Ala Arg Lys Ala Arg Ala Ala Thr Pro Ala Thr Ala Ala Thr Ala
225                 230                 235                 240

Ala Thr Pro Ala Thr Ala Ala Thr Ala Ala Ala
                245                 250

<210> SEQ ID NO 4
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 4

Thr Thr Pro Ala Pro Thr Lys Ala Thr Ala Arg Ala Arg Ala Ala Pro
```

Thr Ala Ala Ala Thr Pro Ala Ala
            20

<210> SEQ ID NO 5
<211> LENGTH: 24
<212> TYPE: PRT
<213> ORGANISM: Artificial Sequence
<220> FEATURE:
<223> OTHER INFORMATION: Synthetic Polynucleotide

<400> SEQUENCE: 5

Ala Ala Ala Ala Ala Thr Ala Thr Ala Ala Ala Arg Arg Ala Ala Ala
1               5                   10                  15

Ala Pro Thr Thr Ala Lys Thr Thr
            20

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
ccgcagtacc cactcaatct                                           20

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
actgcaaagc caaaaccatc                                           20

<210> SEQ ID NO 8
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 8
tacttgttcg ccctcttcg                                            19

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
gtatcttccg gacaggcagt                                           20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
gggacccgca caagcggtgg                                             20

<210> SEQ ID NO 11
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 11
gaggtaaagc caacgcactc                                             20

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
cctgtaaccg caccaagttt                                             20

<210> SEQ ID NO 13
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 13
acccaacgct aaaatcatcg                                             20

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
gcgaaaatgc ccatagtttc                                             20

<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 15
ataccggcga ctgggtttat                                             20

<210> SEQ ID NO 16
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 16
ttgcaaatcg tgggtatgtg t                                           21

<210> SEQ ID NO 17
<211> LENGTH: 20
<212> TYPE: DNA
<213> ORGANISM: Artificial Sequence

```
<220> FEATURE:
<223> OTHER INFORMATION: Synthetic Polynucleotide

<400> SEQUENCE: 17
cttgggtatt tgcacgcatt                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 18
gcaatatcat gccgacacct                                                   20

<210> SEQ ID NO 19
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 19
gggttgcgct cgttgcggga                                                   20

<210> SEQ ID NO 20
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 20

Pro Ala Arg Lys Ala Arg Pro Ala Thr Pro Ala Thr Pro Ala Thr Pro
1               5                   10                  15

Ala Thr Pro Ala Thr Pro Ala Thr
            20

<210> SEQ ID NO 21
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 21

Pro Ala Arg Lys Ala Arg Ala Ala Thr Pro Ala Thr Pro Ala Thr Ala
1               5                   10                  15

Ala Thr Pro Ala Thr Ala Ala Thr Ala Ala Thr Pro Ala Thr Pro Ala
            20                  25                  30

Thr Ala Ala Thr Pro Ala Thr Ala Ala Thr
        35                  40

<210> SEQ ID NO 22
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 22

Ala Ala Thr Pro Ala Thr Pro Ala Thr Ala Ala Thr Pro Ala Thr Ala
1               5                   10                  15
```

Ala Thr

<210> SEQ ID NO 23
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 23

Ala Ala Thr Pro Ala Thr Ala Ala Thr Pro Ala Arg Lys Ala Arg Ala
1               5                   10                  15

Ala Thr Pro Ala Thr Pro Ala Thr
            20

<210> SEQ ID NO 24
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 24

Pro Ala Arg Lys Ala Arg Ala Ala Thr Ala Ala Thr Ala Ala Thr Ala
1               5                   10                  15

Ala Thr

<210> SEQ ID NO 25
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 25

Pro Ala Arg Lys Ala Arg Ala Ala Thr Ala Ala Thr
1               5                   10

<210> SEQ ID NO 26
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 26

Ala Ala Thr Ala Ala Thr Pro Ala Arg Lys Ala Arg Ala Ala Thr Ala
1               5                   10                  15

Ala Thr

<210> SEQ ID NO 27
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 27

Ala Ala Thr Ala Ala Thr Ala Ala Thr Ala Ala Thr Ala Ala Thr Ala
1               5                   10                  15

Ala Thr

<210> SEQ ID NO 28
<211> LENGTH: 24

```
<212> TYPE: PRT
<213> ORGANISM: Artificial Sequence
<220> FEATURE:
<223> OTHER INFORMATION: Synthetic Polypeptide

<400> SEQUENCE: 28

Pro Ala Arg Lys Ala Arg Pro Ala Arg Lys Ala Arg Pro Ala Arg Lys
1               5                   10                  15
Ala Arg Pro Ala Arg Lys Ala Arg
            20

<210> SEQ ID NO 29
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 29

Pro Ala Arg Lys Ala Arg Ala Ala Thr Ala Ala Thr Ala Ala Thr Ala
1               5                   10                  15
Ala Thr Ala Ala Thr Ala Ala Thr Ala Ala Thr Ala Ala Thr
            20                  25                  30

<210> SEQ ID NO 30
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 30

Pro Ala Arg Lys Ala Arg
1               5

<210> SEQ ID NO 31
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 31
ccgcttcaag ggacagtatc tg                                          22

<210> SEQ ID NO 32
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 32
cacgttgtgc accaggaact t                                           21
```